(12) United States Patent
Cooper et al.

(10) Patent No.: US 11,985,930 B2
(45) Date of Patent: May 21, 2024

(54) MOLECULAR BREEDING METHODS

(71) Applicant: PIONEER HI-BRED INTERNATIONAL, INC., Johnston, IA (US)

(72) Inventors: Mark Cooper, Johnston, IA (US); Carlos Messina, Des Moines, IA (US); Frank Technow, Waterloo (CA); Liviu Radu Totir, Johnston, IA (US)

(73) Assignee: PIONEER HI-BRED INTERNATIONAL, INC., IA (US)

( * ) Notice: Subject to any disclaimer, the term of this patent is extended or adjusted under 35 U.S.C. 154(b) by 0 days.

(21) Appl. No.: 15/521,816

(22) PCT Filed: Aug. 4, 2015

(86) PCT No.: PCT/US2015/043525
§ 371 (c)(1),
(2) Date: Apr. 25, 2017

(87) PCT Pub. No.: WO2016/069078
PCT Pub. Date: May 6, 2016

(65) Prior Publication Data
US 2017/0245446 A1   Aug. 31, 2017

Related U.S. Application Data

(60) Provisional application No. 62/093,713, filed on Dec. 18, 2014, provisional application No. 62/069,007, filed on Oct. 27, 2014.

(51) Int. Cl.
| | |
|---|---|
| *A01H 1/04* | (2006.01) |
| *A01K 67/00* | (2006.01) |
| *C12N 15/82* | (2006.01) |
| *C12Q 1/6895* | (2018.01) |
| *G16B 5/00* | (2019.01) |
| *G16B 20/00* | (2019.01) |
| *G16B 20/20* | (2019.01) |
| *G16B 20/40* | (2019.01) |
| *G16B 20/50* | (2019.01) |
| *G16H 50/30* | (2018.01) |
| *G16H 70/60* | (2018.01) |

(52) U.S. Cl.
CPC .............. *A01H 1/04* (2013.01); *A01K 67/00* (2013.01); *C12N 15/8213* (2013.01); *C12Q 1/6895* (2013.01); *G16B 5/00* (2019.02); *G16B 20/00* (2019.02); *G16B 20/20* (2019.02); *G16B 20/40* (2019.02); *G16B 20/50* (2019.02); *C12Q 2600/13* (2013.01); *C12Q 2600/156* (2013.01); *G16H 50/30* (2018.01); *G16H 70/60* (2018.01); *Y02A 90/10* (2018.01)

(58) Field of Classification Search
None
See application file for complete search history.

(56) References Cited

U.S. PATENT DOCUMENTS

| | | | |
|---|---|---|---|
| 2005/0144664 A1* | 6/2005 | Smith | A01H 1/02 800/266 |
| 2008/0163824 A1 | 7/2008 | Moser et al. | |
| 2010/0095394 A1* | 4/2010 | Bink | G06F 19/18 800/264 |
| 2011/0098195 A1 | 4/2011 | Russwurm | |
| 2014/0220568 A1 | 8/2014 | Inze et al. | |

FOREIGN PATENT DOCUMENTS

| | | |
|---|---|---|
| CN | 101710362 A | 5/2010 |
| WO | 2009108802 A2 | 9/2009 |
| WO | 2014200348 A1 | 12/2014 |
| WO | 2015155607 A2 | 10/2015 |

OTHER PUBLICATIONS

Schulz-Streeck et al., 2012, Crop Science 52: 2453-2461.*
Rincent et al., 2012, Genetics 192: 715-728.*
Ochs, 2012, Knowledge-based data analysis comes of age, Briefing in Bioinformatics II: 30-39.*
Weckwerth, 2011, Green Systems Biology—From Single Genomes, Proteomes and Metabolomes to Ecosystems Research, Journal of Proteomics 75: 284-305.*
Csillery et al 2010 Trends in Ecology and Evolution 25:410-418, provided by Applicant (Year: 2010).*
Belhaj, K. et al., "Plant genome editing made easy: targeted mutagenesis in model and crop plants using the CRISPR/Cas system", 2013, Plant Methods, vol. 9(1): 39.
Fan, L. et al., "Urinary sodium excretion and kidney failure in nondiabetic chronic kidney disease", 2014, Kidney International, 86, 582-288.
Goldstein, L.J. et al., "A computer model of the kidney", 1992, Computer Methods and Programs in Biomedicine, 37, 191-203.
Thiele, I. et al., "A community-driven global reconstruction of human metabolism", 2013, Nature Biotechnology, vol. 31(5): 419-425.
Uttamsingh, R.J. et al., "Mathematical model of the human renal system", 1985, Medical & Biological Engineering & Computing, 525-535.
Zhao, Y. et al., "Impact of selective genotyping in the training population on accuracy and bias of genomic selection", 2012, Theoretical and Applied Genetics, vol. 125(4): 707-713.
International Search Report and Written Opinion of the International Searching Authority for Application PCT/US15/43525, dated Dec. 30, 2015.

(Continued)

*Primary Examiner* — Brent T Page

(57) ABSTRACT

Improved molecular breeding methods include a method in which an association data set is developed by associating the phenotypes of a broad population of individuals with the individual genotypes. The association data set is used in conjunction with a growth model in order to select breeding pairs likely to generate offspring with one or more desirable traits.

16 Claims, 29 Drawing Sheets

(56) References Cited

OTHER PUBLICATIONS

Beaumont et al. "The Bayesian revolution in genetics", Nature Reviews Genetics. Apr. 1, 2004 (Apr. 1, 2004) 5(4): 251-261.
Csillery et al. "Approximate Bayesian Computation (ABC) in practice", Trends in Ecology and Evolution. Jul. 1, 2010 (Jul. 1, 2010) 25 (7): 410-418.
Habier et al. "Genomic BLUP Decoded: A Look into the Black Box of Genomic Prediction", Genetics. May 2, 2013 (May 2, 2013), 194 (3): 597-607.
Messina et al. "Yield-trait performance landscapes: from theory to application in breeding maize for drought tolerance", Journal of Experimental Botany. Jan. 1, 2011 (Jan. 1, 2011) 62(3): 855-868.
Stahl et al. "Bayesian inference analyses of the polygenic architecture of rheumatoid arthritis", Nature Genetics. May 1, 2012 (May 1, 2012), 44(5): 483-489.
Zhong and Jannink. "Using Quantitative Trait Loci Results to Discriminate Among Crosses on the Basis of Their Progeny Mean and Variance", Genetics. (Sep. 2007) 177: 567-576.
Jarquín, D, et al.: "A reaction norm model for genomic selection using high-dimensional genomic and environmental data," Theor Appl Genet, 2014, 127(3):595-607. Epub Dec. 12, 2013.
Muchow, R.C., et al.: "Temperature and Solar Radiation Effects on Potential Maize Yield across Locations," Agron J., 1990, 82:338-343.
Extended European Search Report for European Application No. 15853669.8, mailed Aug. 28, 2018, 10 Pages.
International Preliminary Report on Patentability for International Application No. PCT/US2015/043525, mailed May 11, 2017, 10 Pages.
Partial Supplementary European Search Report for European Application No. 15853669.8, mailed May 14, 2018, 9 Pages.

\* cited by examiner

MOLECULAR BREEDING METHODS

CROSS REFERENCE TO RELATED APPLICATIONS

This application is the National Stage filing under 35 U.S.C. § 371 of International Application No. PCT/US15/43525, filed on Aug. 4, 2015, which claims the benefit of priority to U.S. Provisional Application No. 62/069,007, filed on Oct. 27, 2014 and U.S. Provisional Application No. 62/093,713, filed Dec. 18, 2014, the contents of which are herein incorporated by reference in their entirety.

BACKGROUND

Molecular breeding techniques involve associating a genetic feature (genotype) with a phenotypic trait (phenotype). Breeding cycles can be accelerated because a genotype can be determined more quickly than a phenotype. Genomic prediction is used in plant and animal breeding to predict breeding values for selection purposes, and in human genetics to predict disease risk. Genomic prediction methods rely on a dataset (the "training dataset") of phenotypes of a set of individuals (the "training individuals") and associated genotypic data, typically over many genetic markers. Statistical methods are used with the training dataset in combination with the genotype of a selection candidate to predict its breeding value or disease risk. Often, however, conventional genomic prediction methods such as the popular GBLUP method fail to make accurate predictions for complex traits under the influence of non-linear genetic effects, such as conveyed by non-linear relationships between output traits and underlying component traits within environments and also genotype-by-environment interactions that further extend the complexity of the non-linear relationships with the component traits. There is thus a need in the genomic prediction arts for improved genomic predictions, particularly for selection of candidates for complex traits when they have a non-linear relationship with the component traits and also genotype-by-environment interactions.

SUMMARY

An embodiment includes a method for selecting individuals in a breeding program, said method comprising: planting and growing a genetically diverse or genetically narrow population of training individuals; phenotyping the genetically diverse or genetically narrow population of training individuals to generate a phenotype training data set; associating the phenotype training data set with a genotype training data set comprising genetic information across the genome of each training individual a biological model such as a crop growth model, a method for estimating effects of genotypic markers and a method for linking the estimation of effects of genotypic markers with the biological model: genotyping a genetically diverse population of breeding individuals; predicting the trait performance of the breeding individuals using the association training data set, a biological model such as a crop growth model, a method for estimating effects of genotypic markers and a method for linking the estimation of effects of genotypic markers with the biological model: selecting breeding pairs from the genetically diverse population of breeding individuals based plant genotypes using the association training data set and a growth model to select breeding pairs likely to generate offspring with one or more desired traits; crossing the breeding pairs to generate offspring; and growing the offspring with the one or more desired traits.

In another embodiment, the method may be used to map quantitative trait loci (QTL), which may then be used in a marker assisted selection strategy.

DESCRIPTIONS OF THE FIGURES

Figure 7:
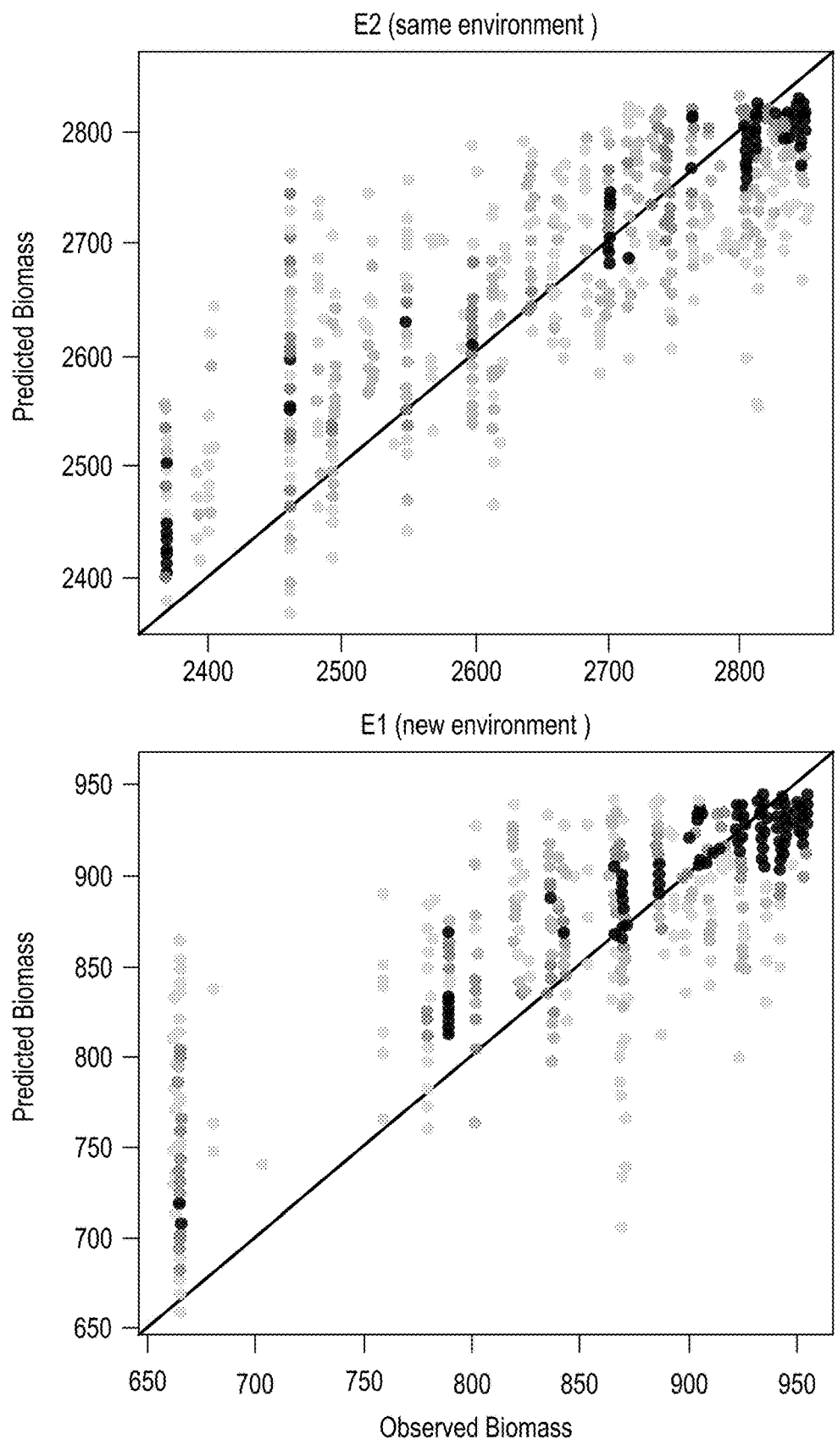

FIG. 7 is a graph of observed and predicted biomass yield of the validation set DH lines in environments E1 and E2. The method used was ABC. Phenotypic data from E2 was used for estimation (but of different DH lines).

Figure 8:
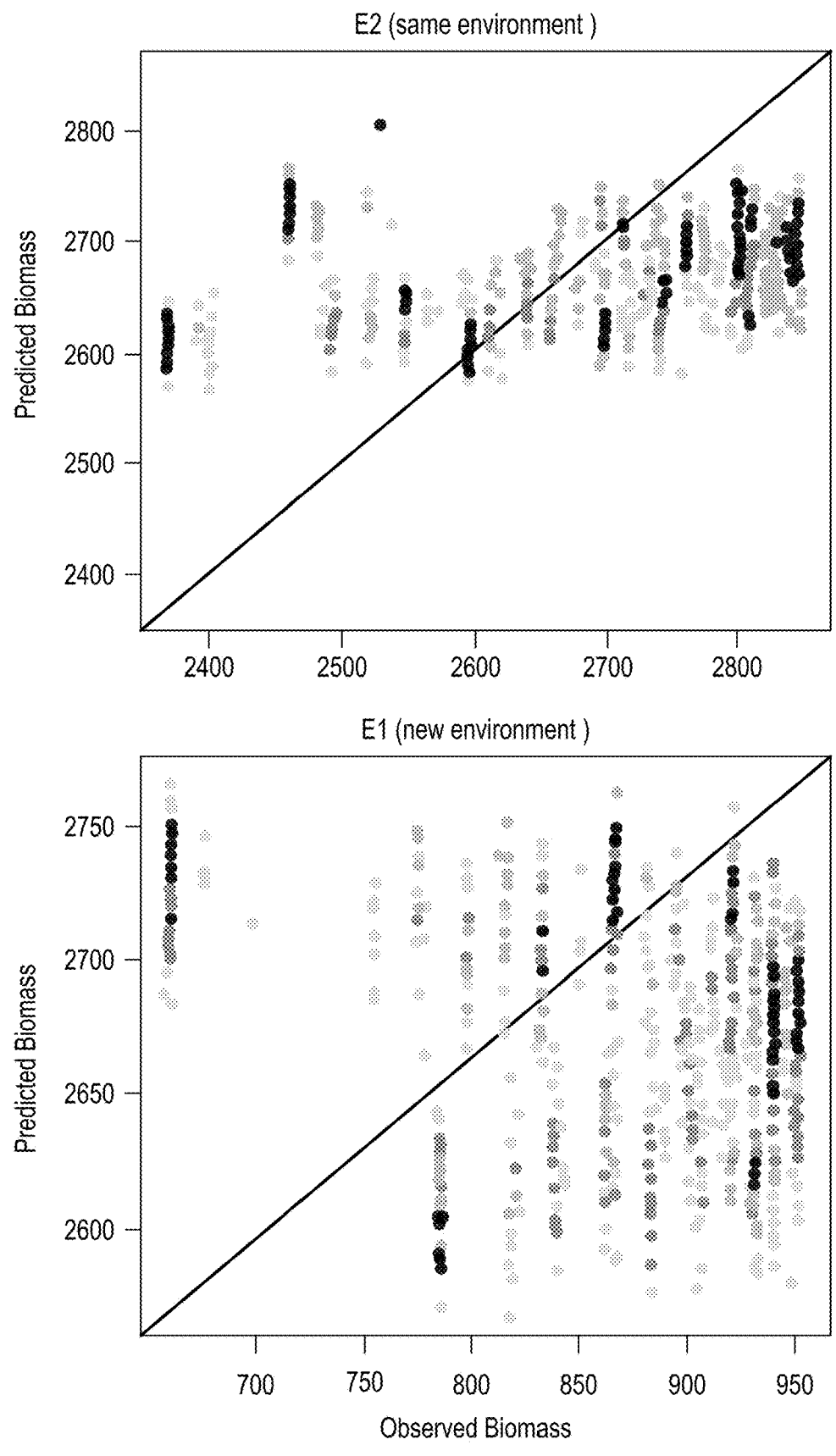

FIG. 8 is a graph of observed and predicted biomass yield of the validation set DH lines in environments E1 and E2. The method used was GBLUP. Phenotypic data from E2 was used for estimation (but of different DH lines).

Figure 9:
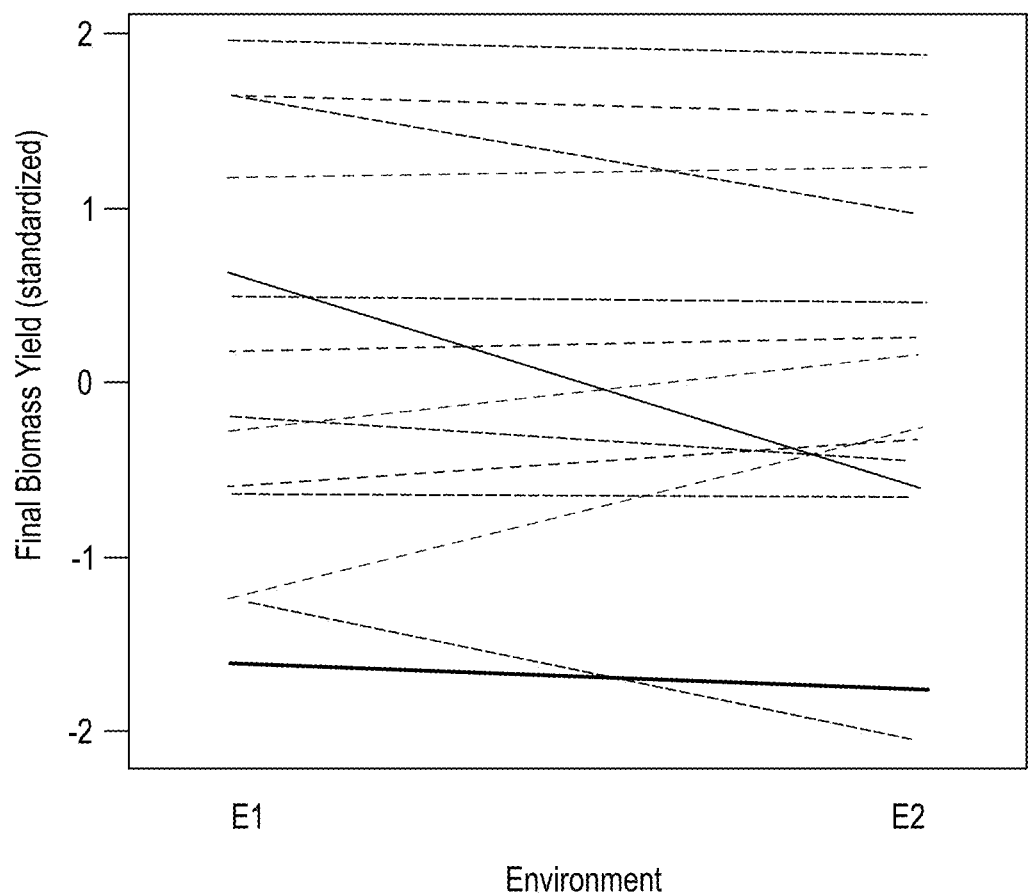

FIG. 9 is an interaction plot of final biomass yield of 25 representative DH lines in environment E1 and E2. The final biomass yield values were standardized within each environment to improve visualization.

Figure 10:
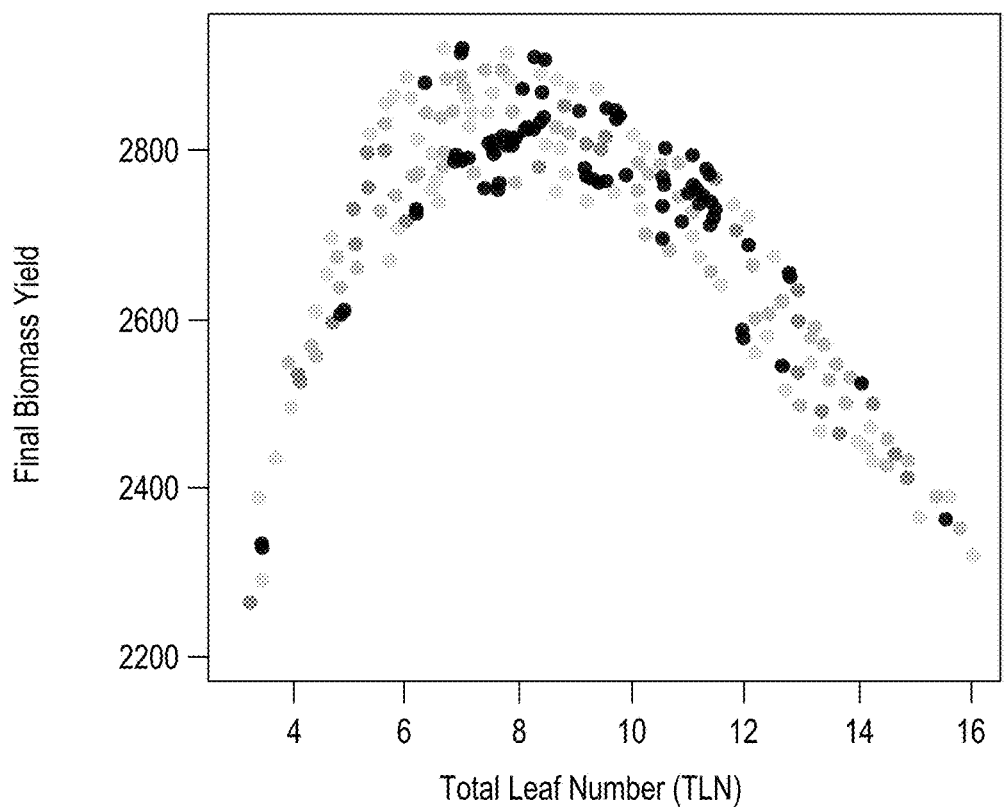
Figure 10:
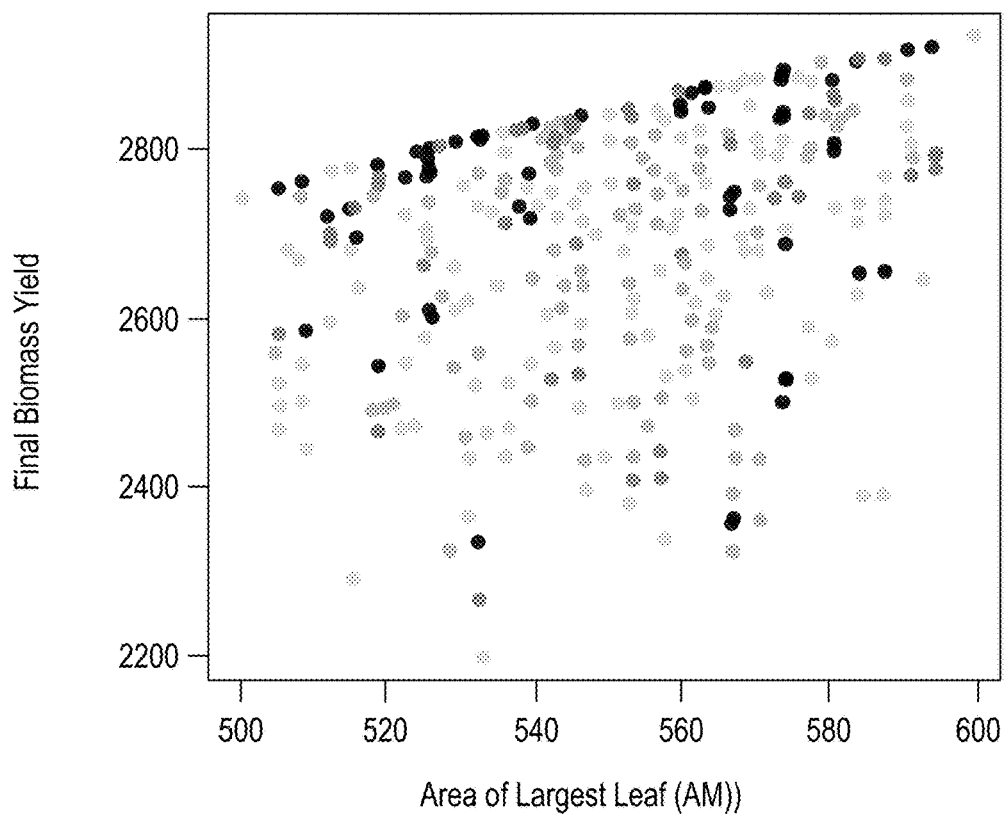

FIG. 10 is a scatterplot of final biomass yield (BM) in environment E2 and Total Leaf Number (TLN) and Area of Largest Leaf (AM), respectively, for 2,000 DH lines in a representative example.

Figure 11:
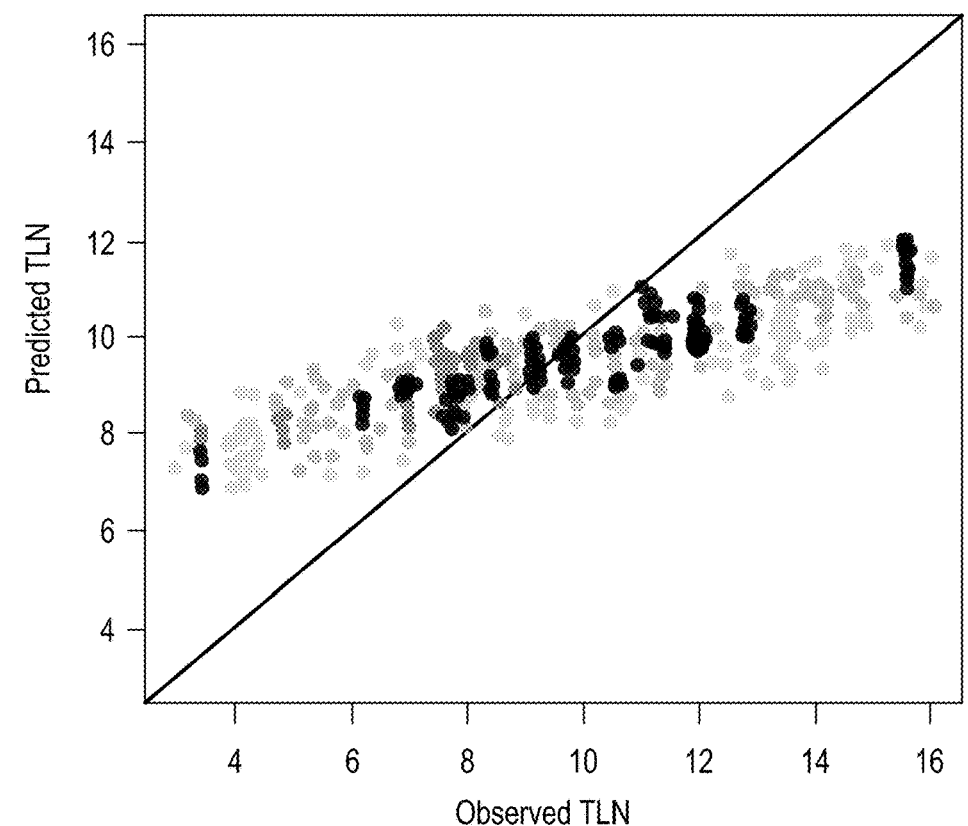
Figure 11:
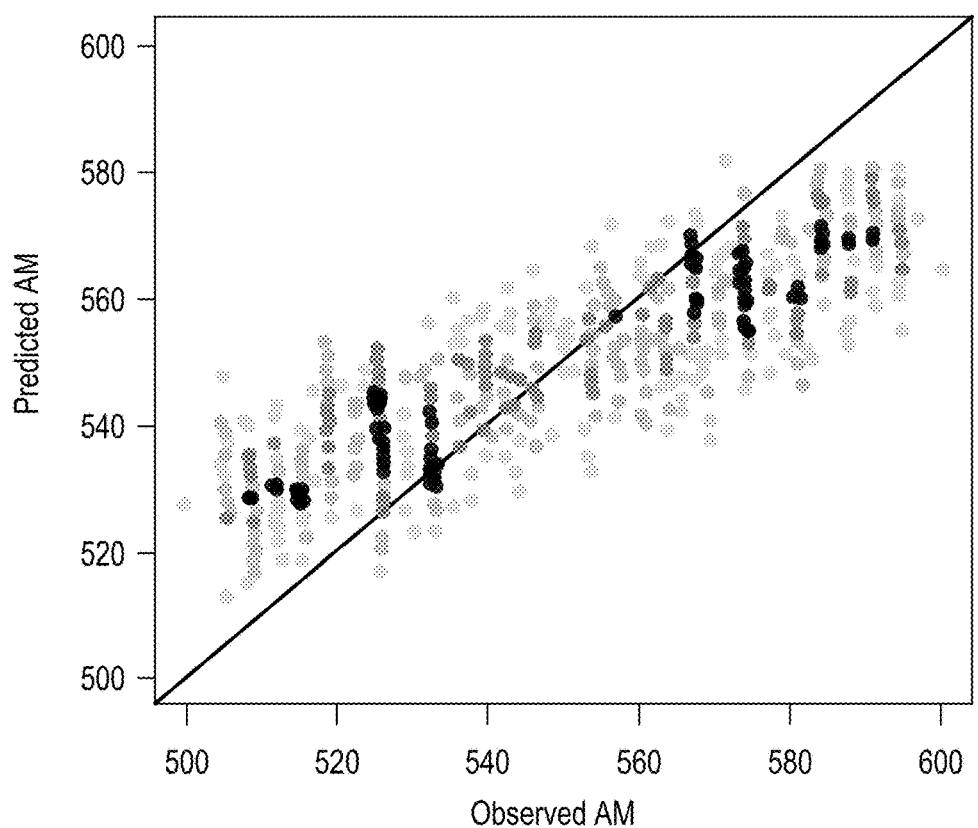

FIG. 11 is a graph of predicted vs. observed TLN and AM values of DH lines in the validation set for method ABC-CGM. In this particular example, the correlation between predicted and observed values was 0.86 (TLN) and 0.88 (AM). For comparison, with GBLUP the correlations were −0.28 (TLN) and 0.63 (AM).

Figure 12:
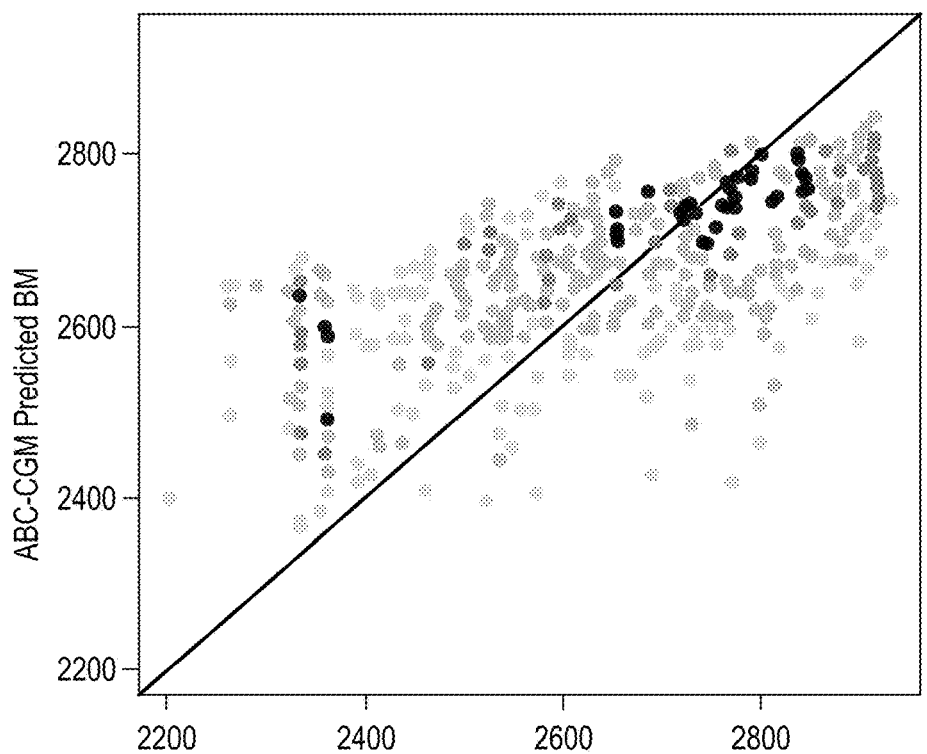
Figure 12:
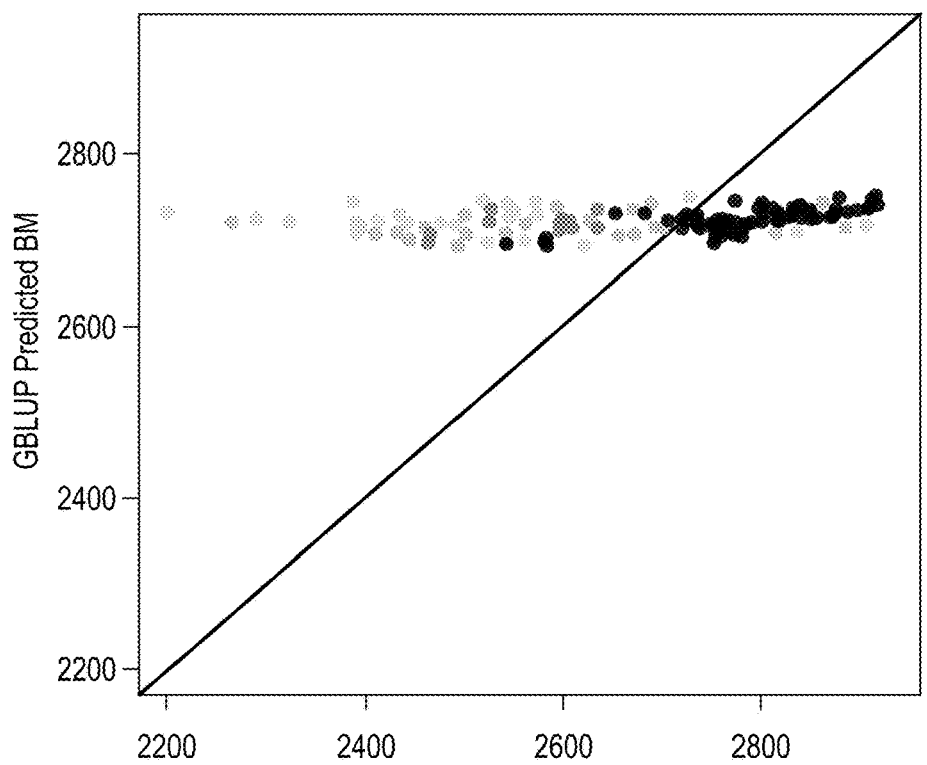
Figure 12:
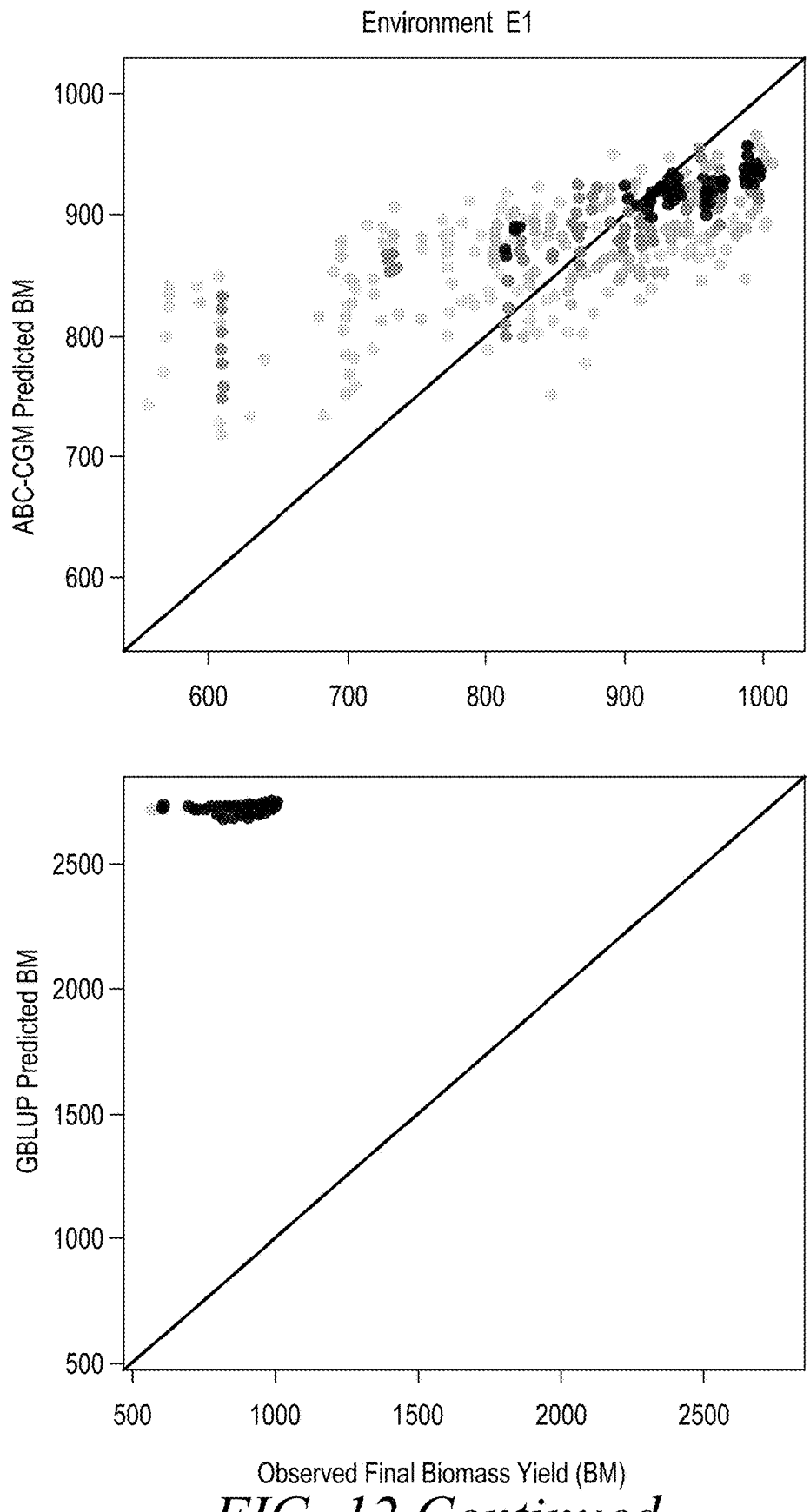

FIG. 12 is a graph of predicted vs. observed final biomass yield (BM) of DH lines in the validation set, in environments E2 and E1, obtained with methods ABC-CGM and GBLUP. In this particular example, the correlation between predicted and observed values for ABC-CGM was 0.75 (E2) and 0.79 (E1) and for GBLUP 0.28 (E2) and 0.15 (E1).

Figure 13:
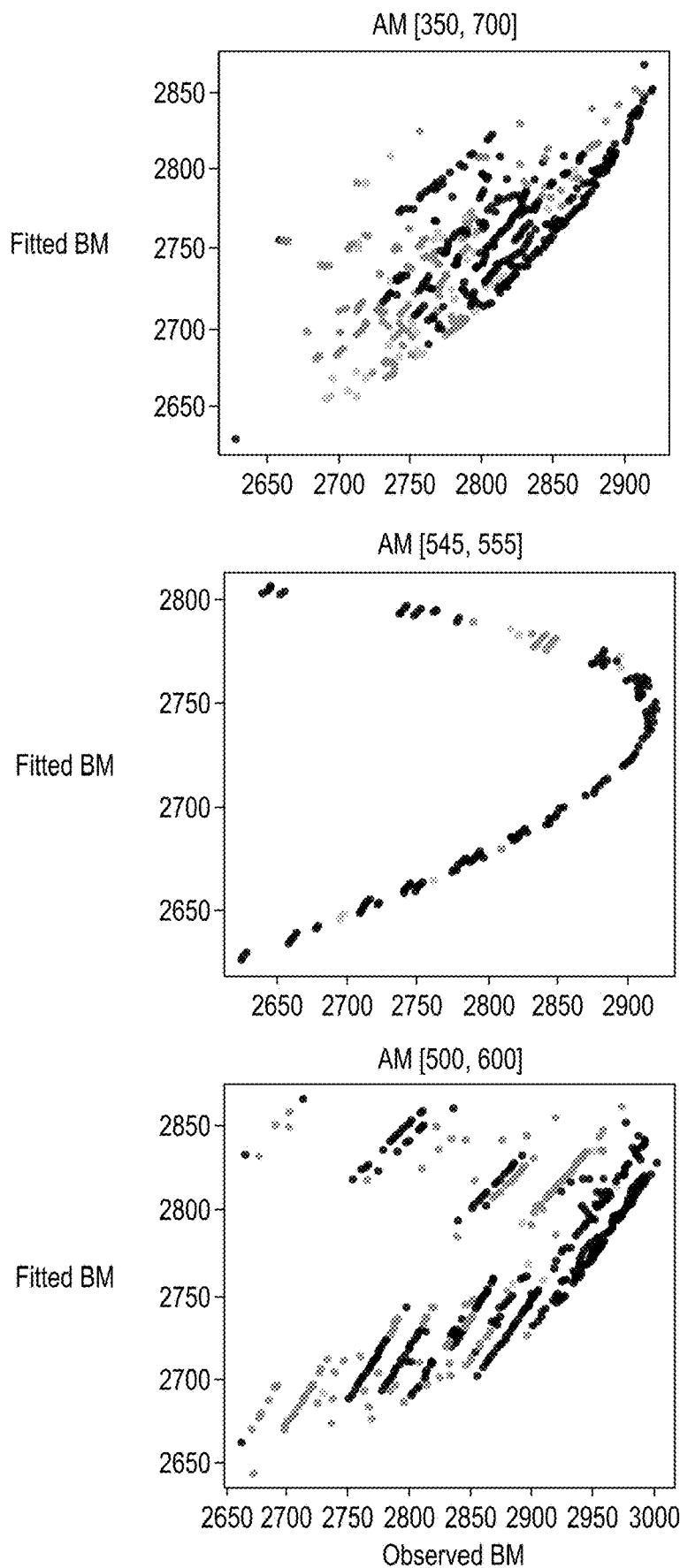

FIG. 13 is a graph of observed final biomass yield (BM) in environments E2 vs. fitted values from model BM~TLN+AM for different value ranges of AM.

Figure 14:
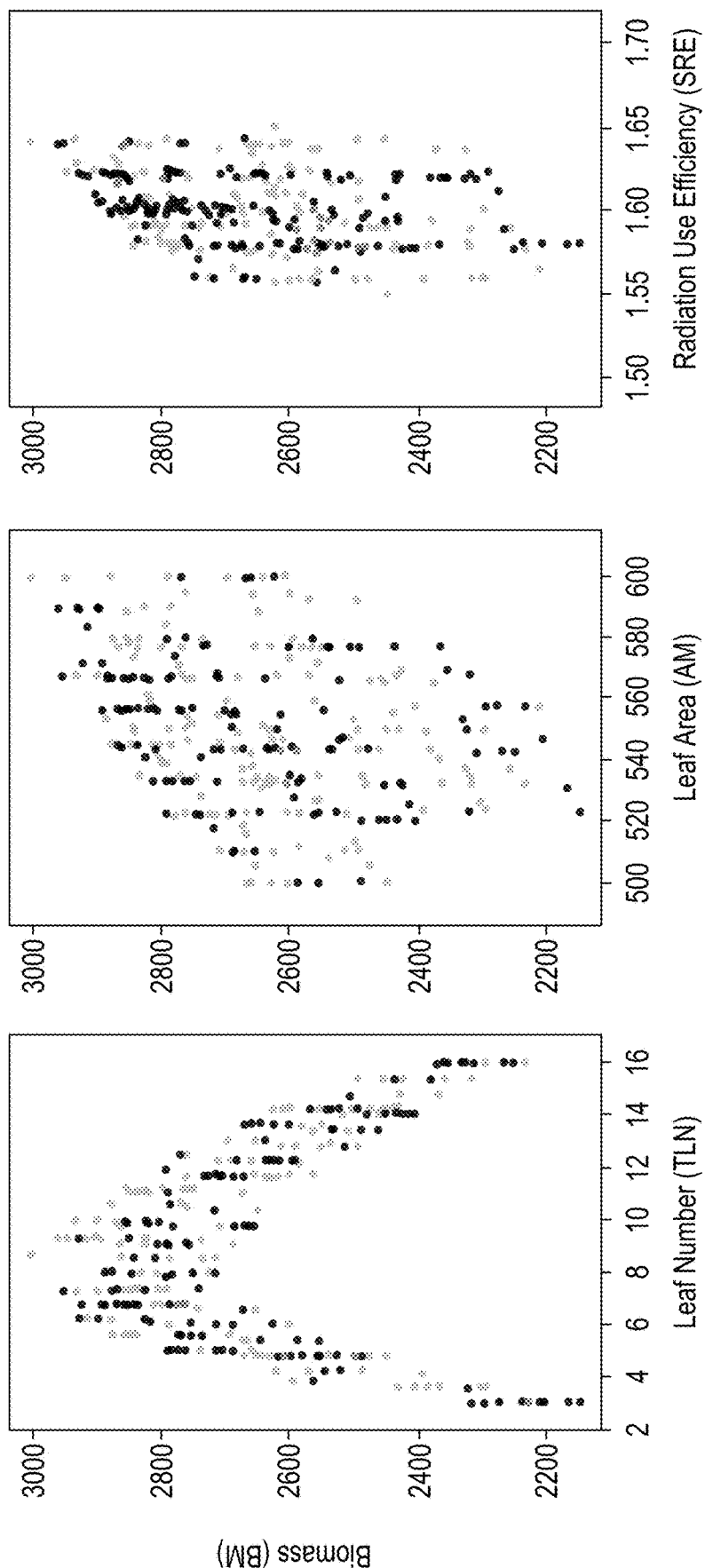

FIG. 14 is a graph of predicted vs. observed values of physiological traits in the validation set. Predictions were obtained using ABC-CGM with optimal parameter settings.

Figure 15:
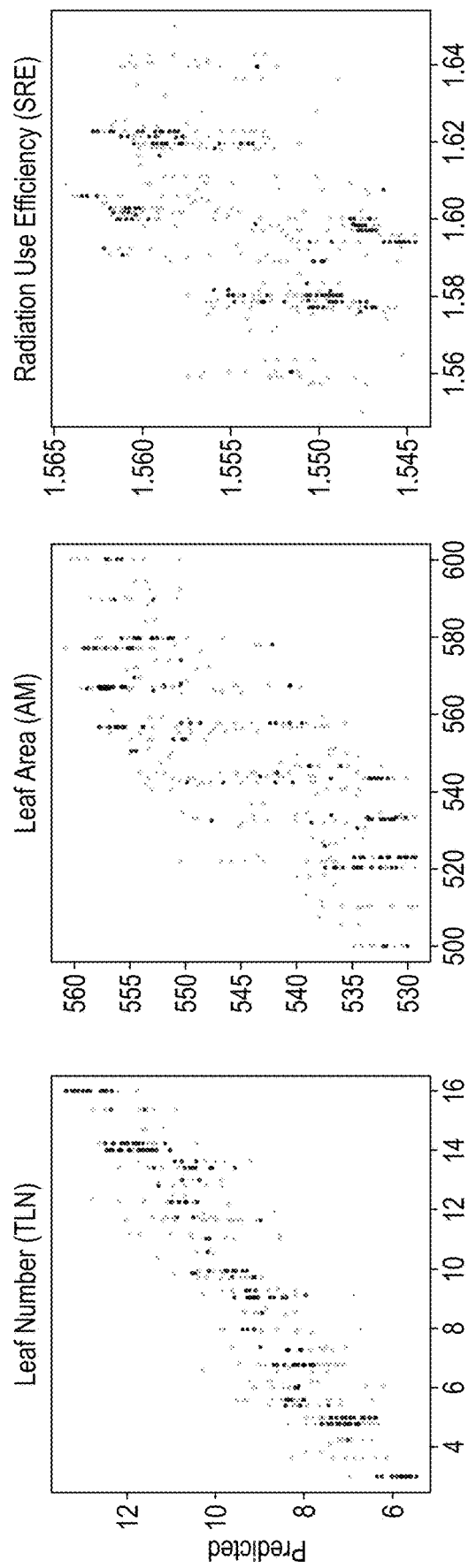

FIG. 15 is a graph of predicted vs. observed values of physiological traits in the validation set. Predictions were obtained using ABC-CGM. (representative example).

Figure 16:
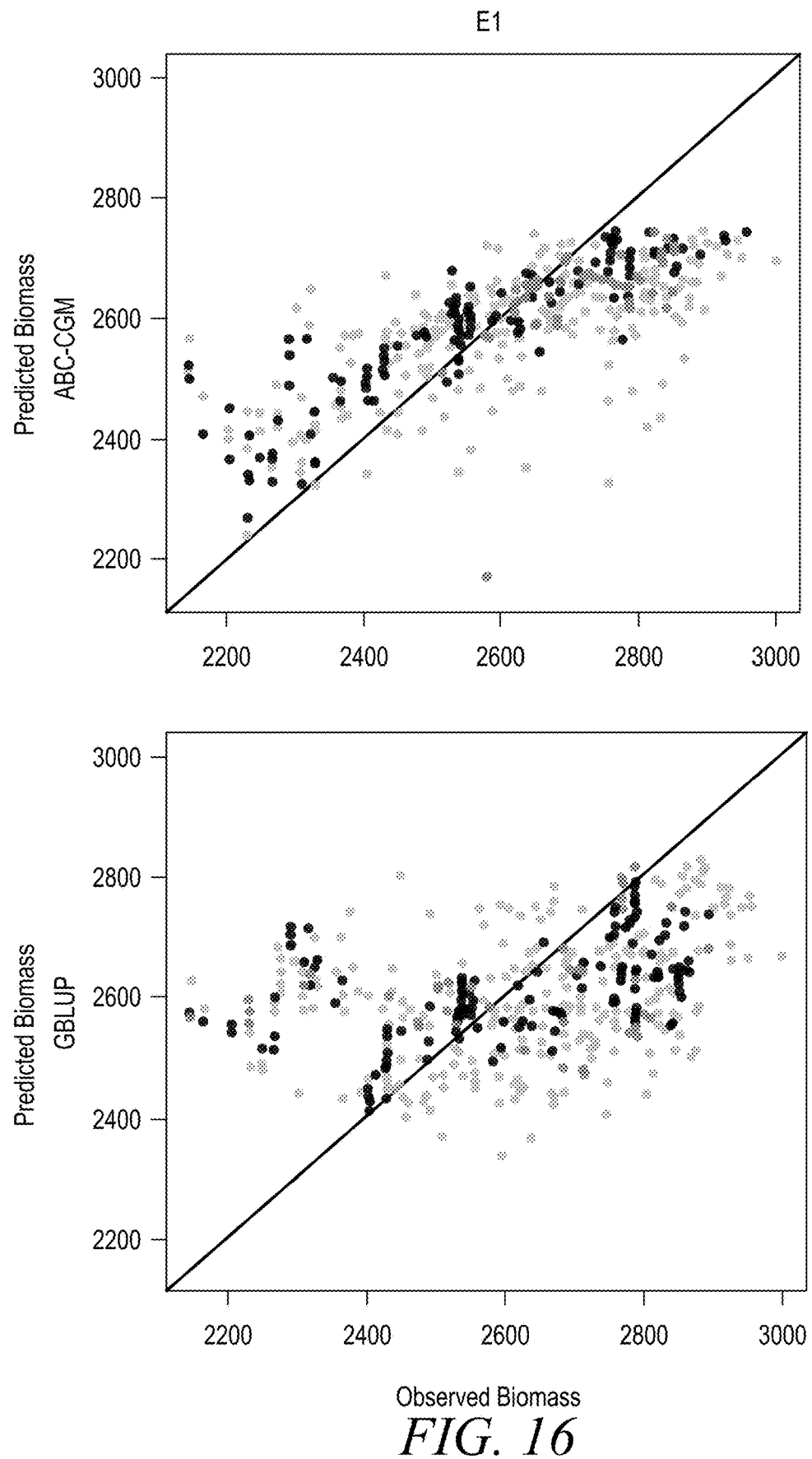
Figure 16:
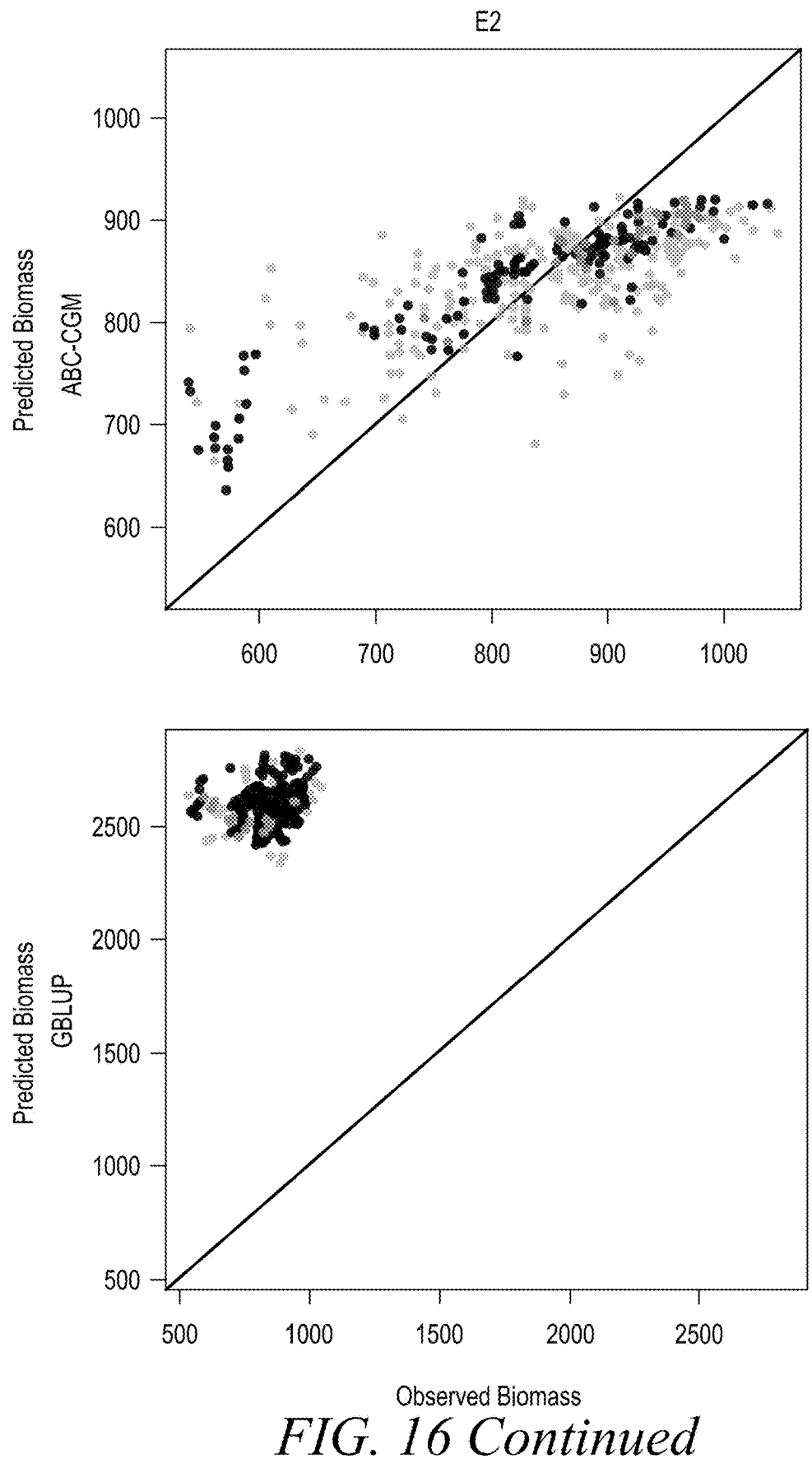

FIG. 16 is a graph of predicted vs. observed final biomass (BM) values in the validation set for environments E1 and E2. Predictions were obtained with ABC-CGM (row 1) and GBLUP (row 2).

Figure 17:
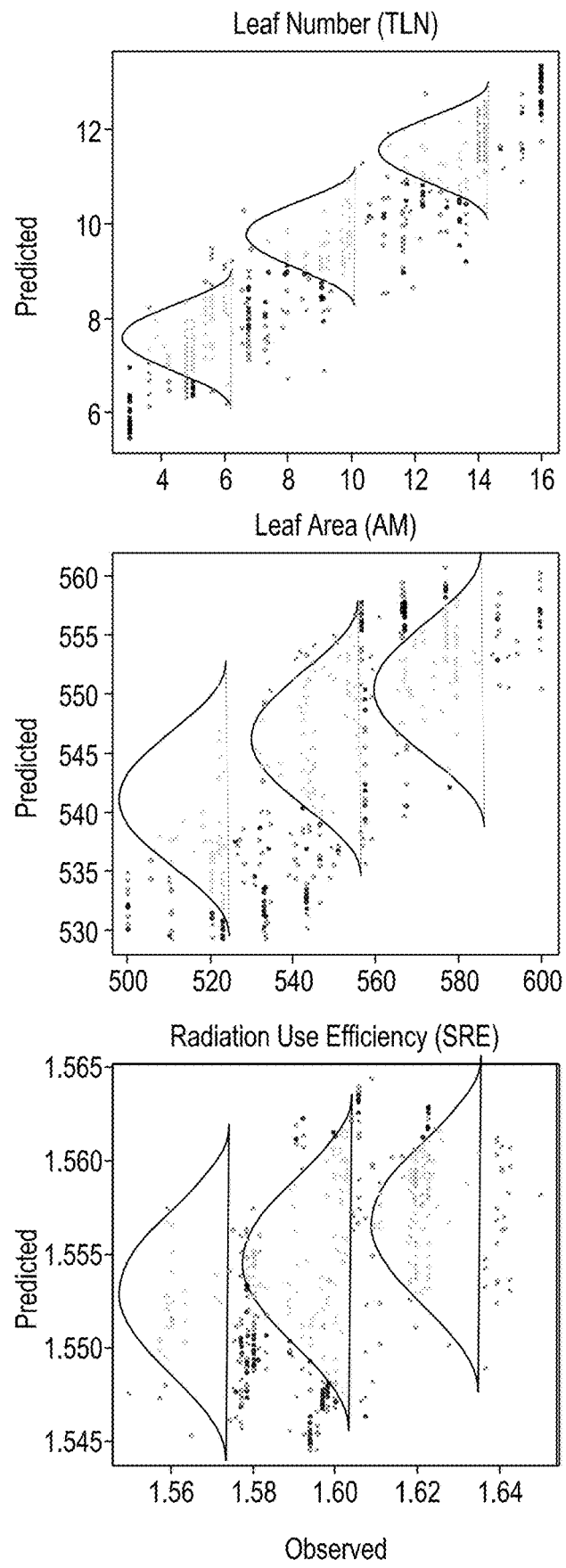

FIG. 17 is a graph of predicted vs. observed values of physiological traits in the validation set (see FIG. 15). The bell-curves illustrate the uncertainty in parameter estimates in terms of prediction error.

Figure 18:
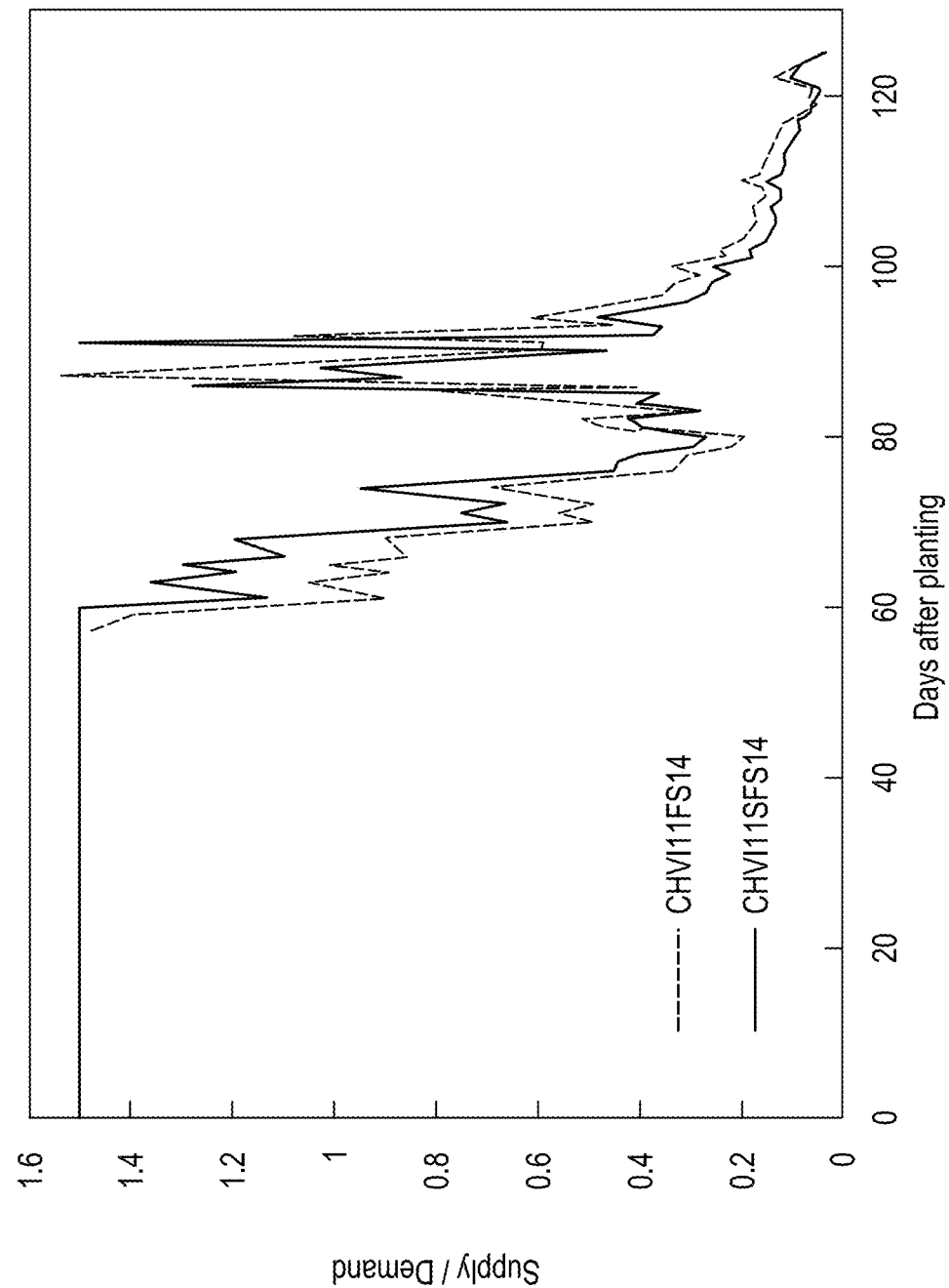

FIG. 18 is the temporal pattern of modeled water supply/demand ratio for two drought environments. The time period of flowering, measured as the time of pollen shed, for entries is indicated for both environments by the horizontal bars at approximately 80 days after planting.

Figure 19:
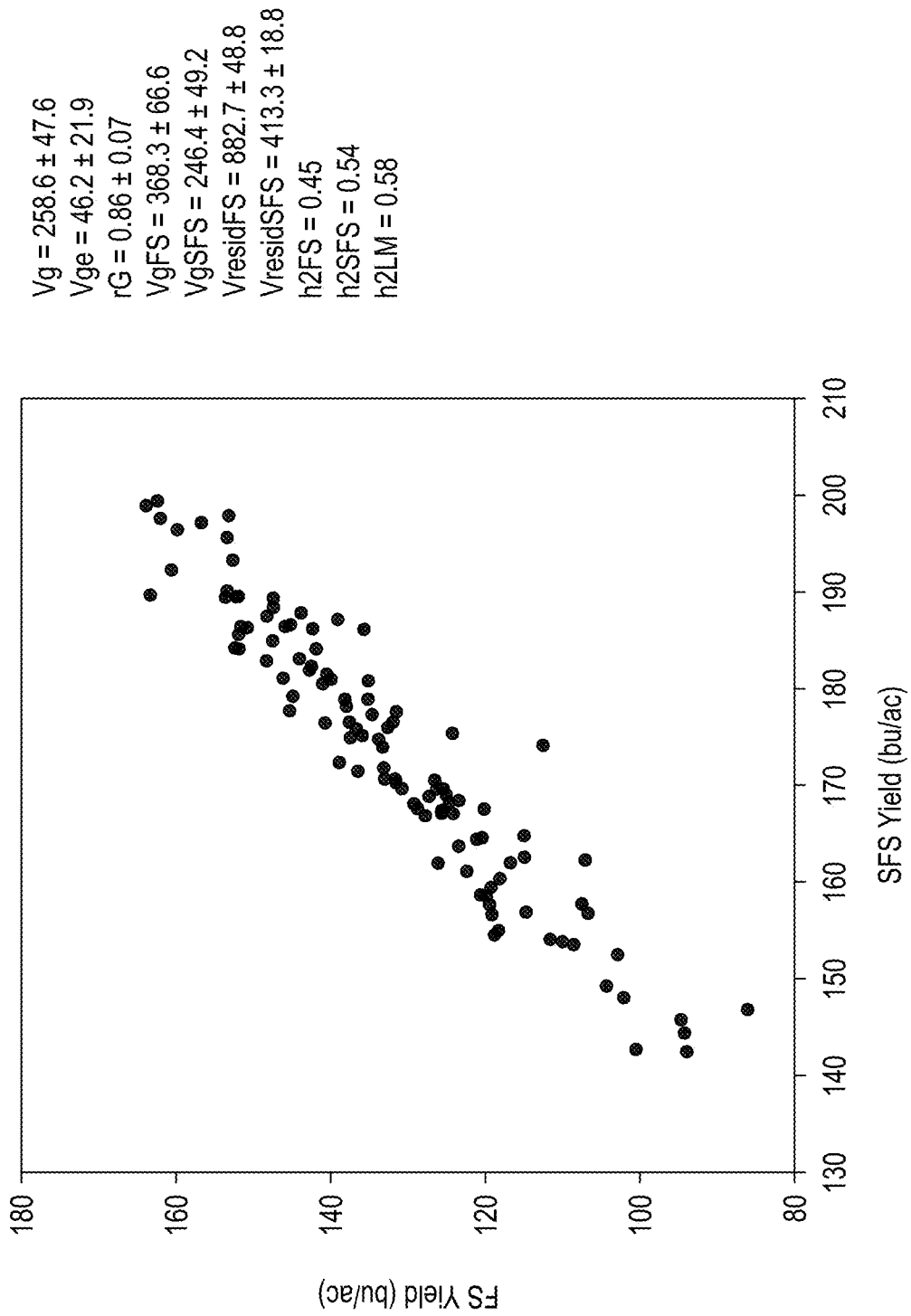
Figure 20B:
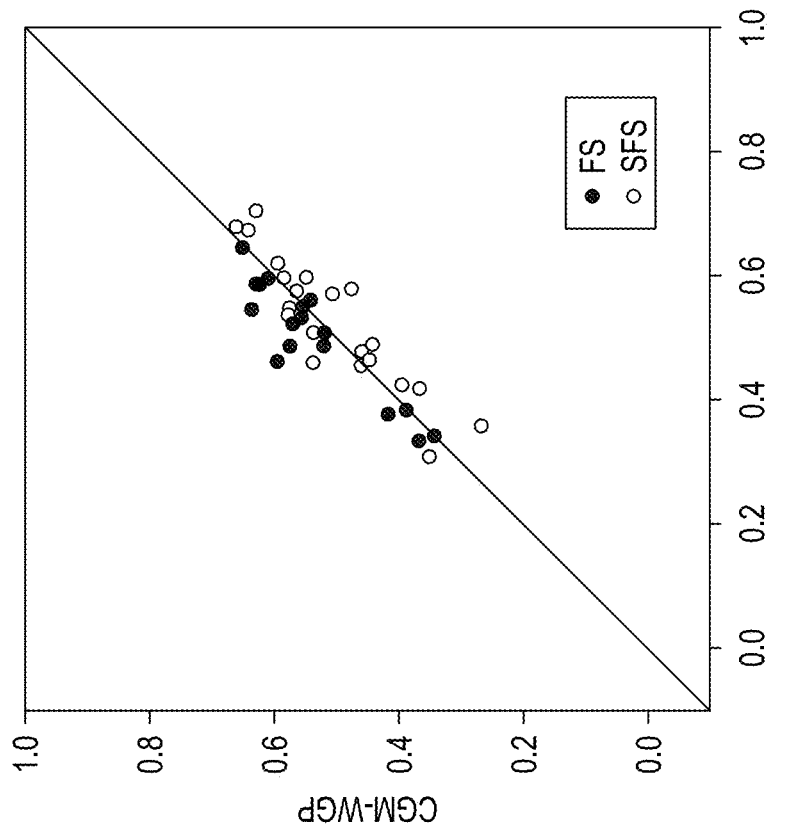
Figure 20A:
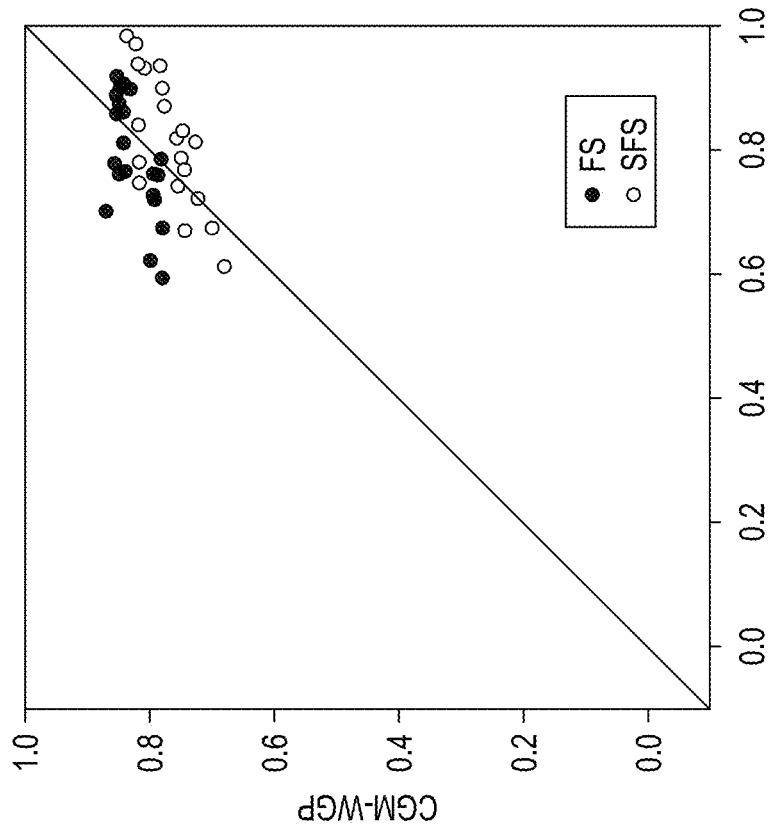
Figure 20C:
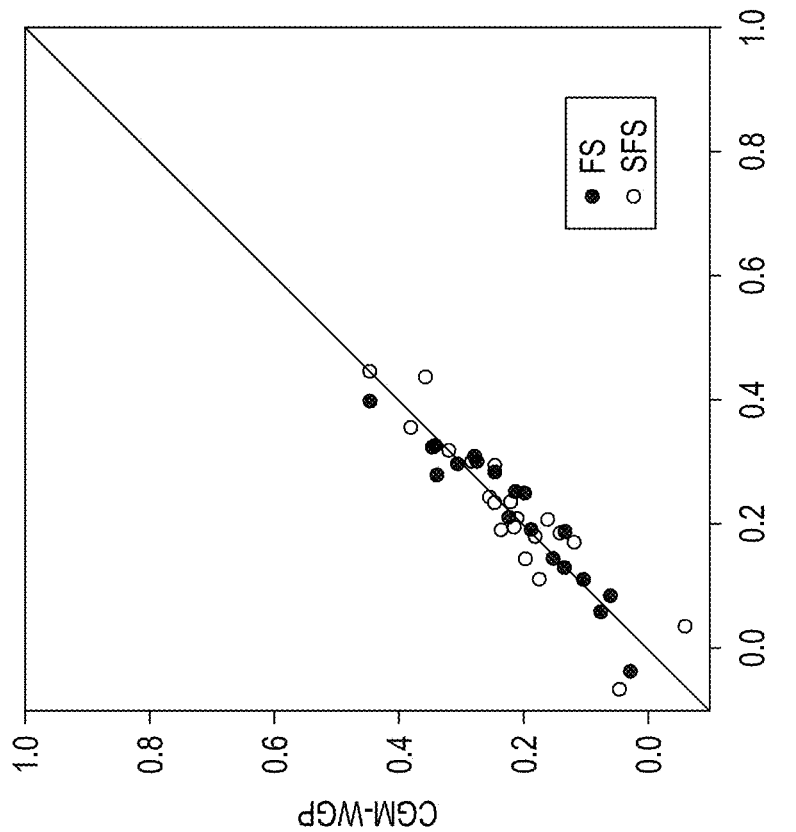
Figure 20D:
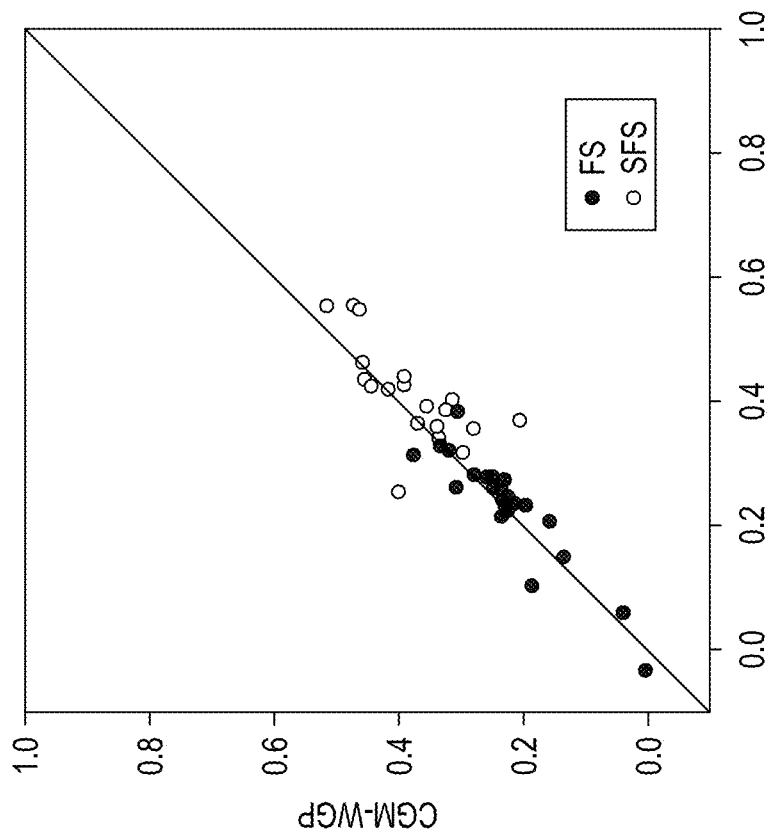

FIG. 19 shows grain yield BLUPs for the complete set of DH entries evaluate in the two drought environments.

FIG. 20 shows a comparison of prediction accuracy obtained for testcross grain yield between CGM-WGP and GBLUP for 20 replications for a single maize cross evaluated in two drought environments: 20a Estimation Entries in Observed Environments, 20b Estimation Entries in New Environments, 20c Test Entries in Observed Environments, 20d Test Entries in New Environments. Legend identifies the environment where genetic model parameters were estimated.

FIG. 21 shows one replication of grain yield predictions based on CGM-WGP and GBLUP for the Test set of 56 DH entries in the FS prediction environment based on model selection in the SFS estimation environment using the Estimation set of 50 DH entries.

Figure 22:
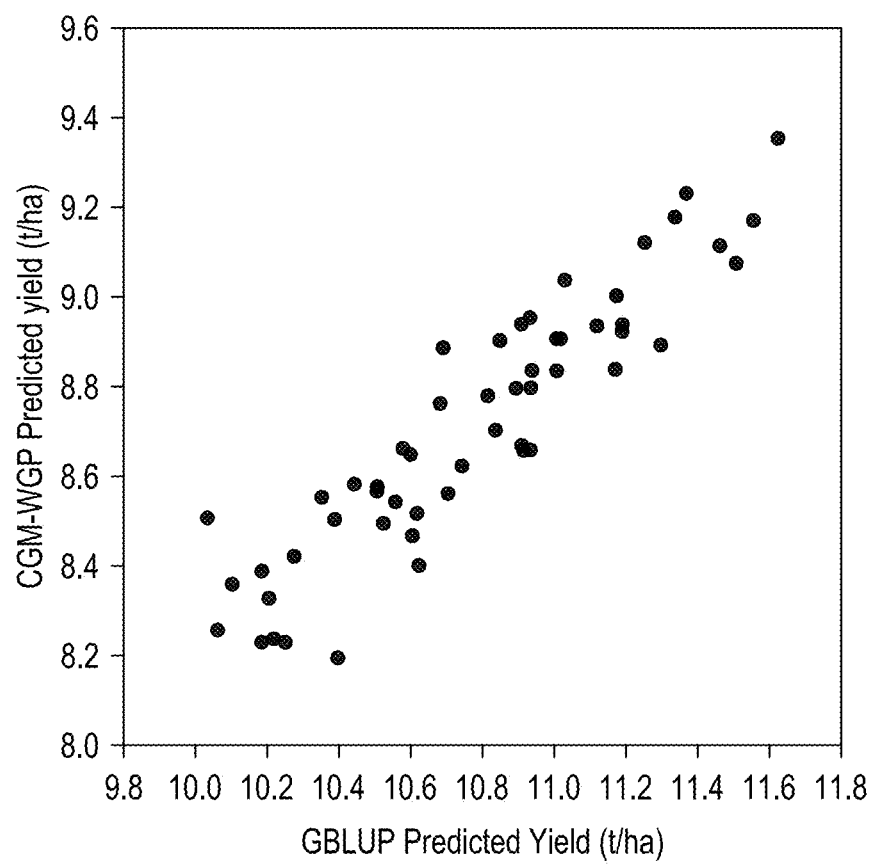

FIG. 22 shows a comparison of grain yield predictions based on GBLUP and CGM-WGP for one replication.

Figure 23A:
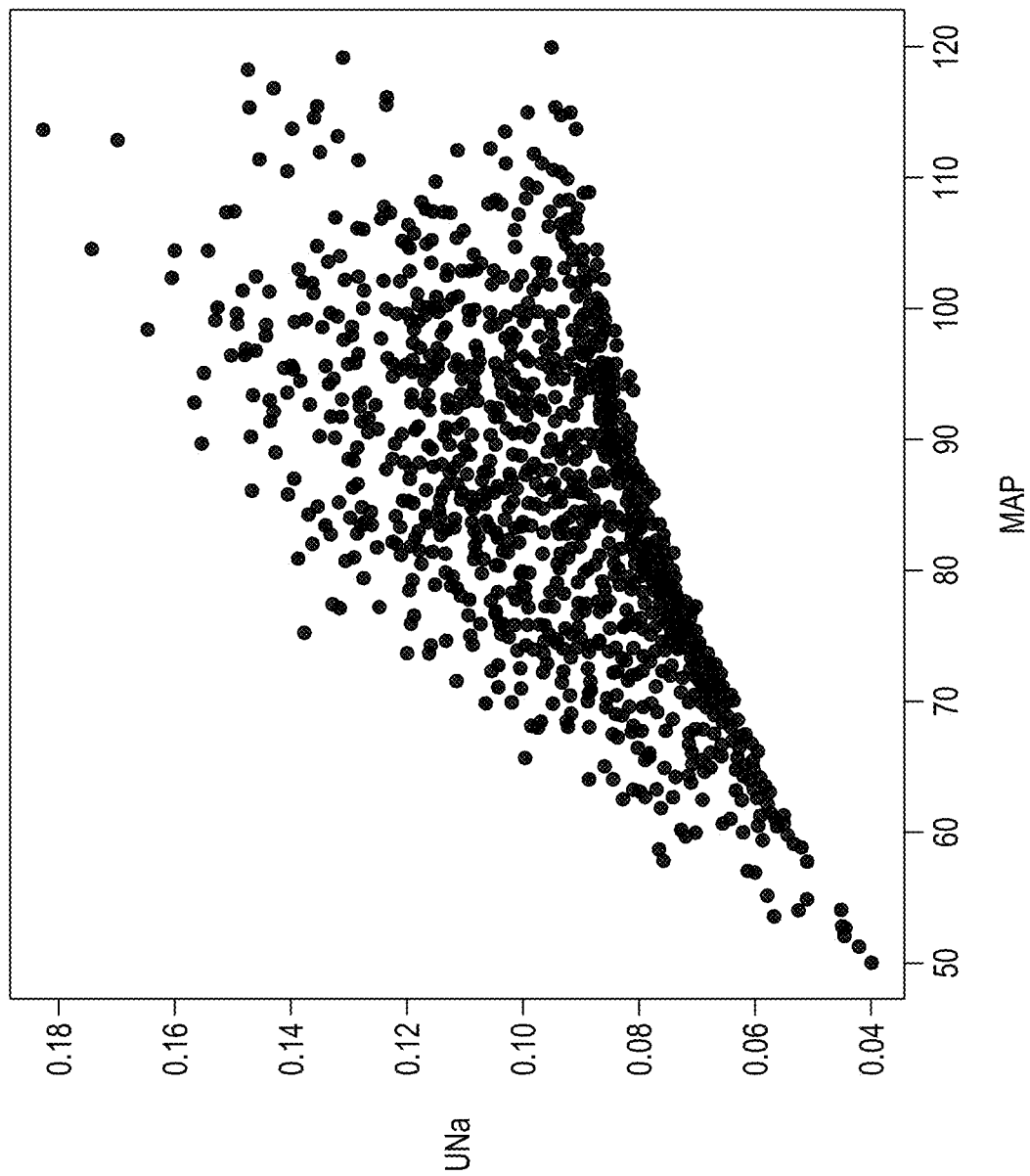
Figure 23B:
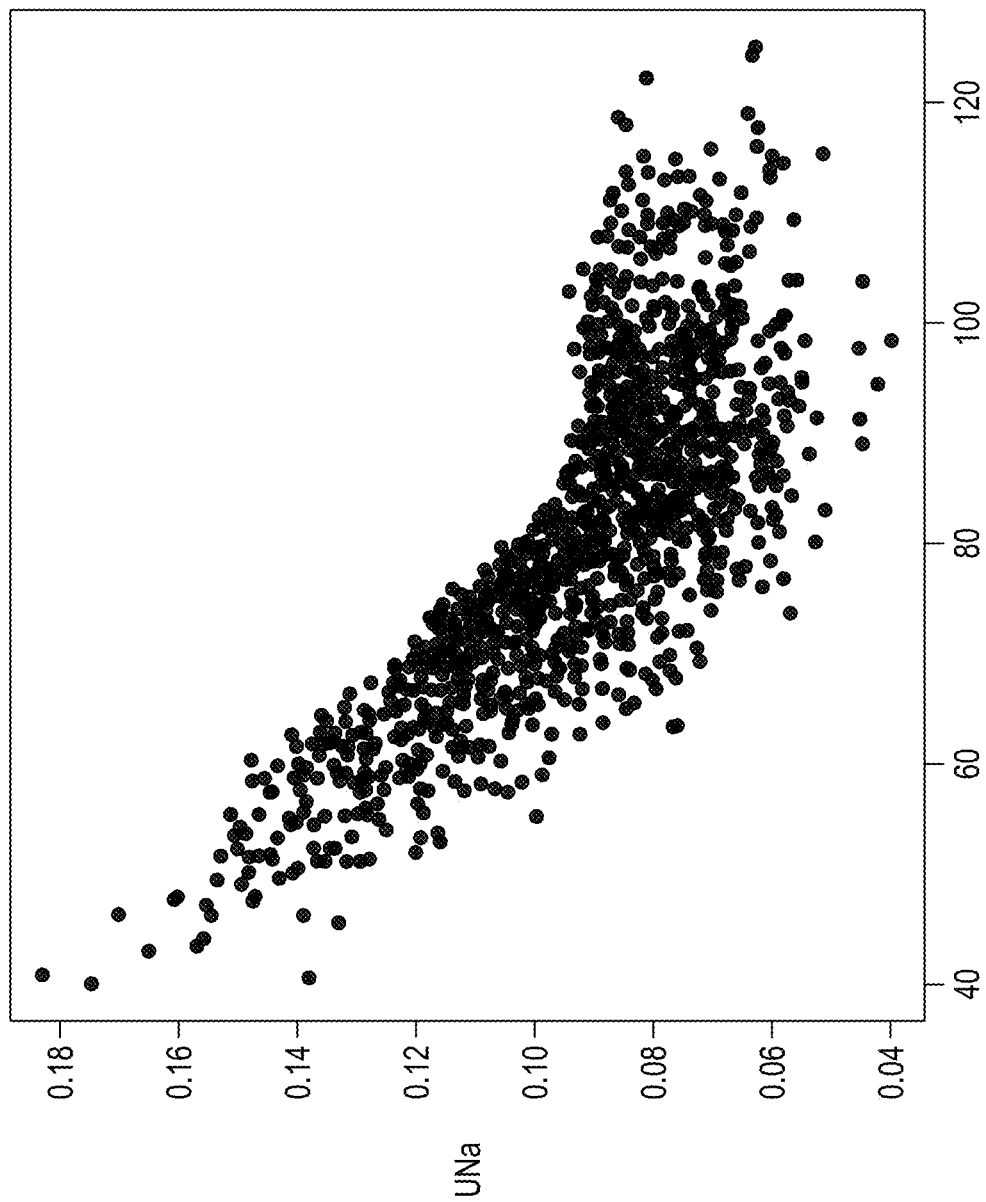
Figure 23C:
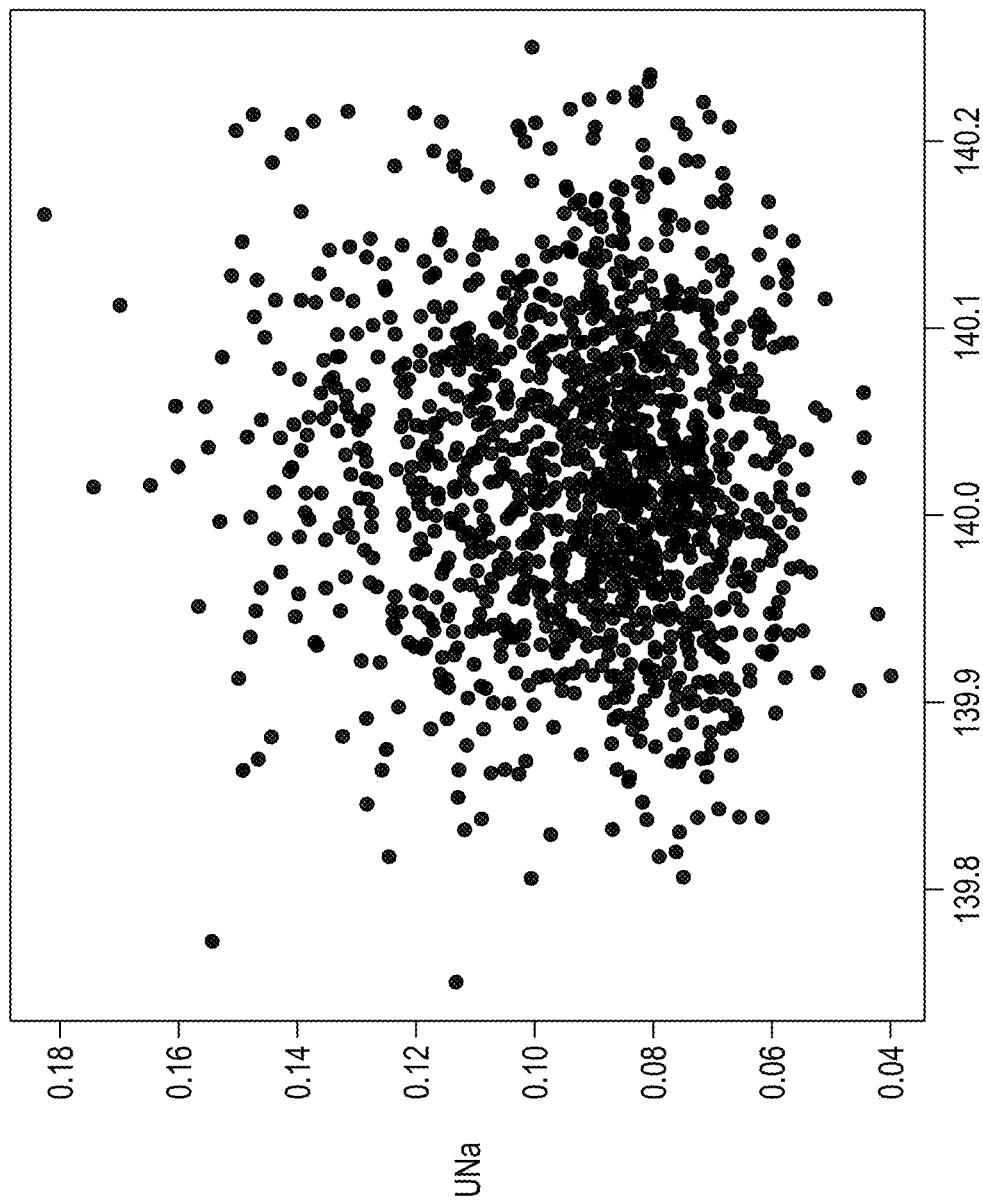

FIG. 23 shows urinary sodium excretion (UNa, mEq/l) as a function of mean arterial blood pressure (MAP, mmHg), aldosterone concentration (ALD, ng/l) and serum sodium (SNa mEq/l).

Figure 24:
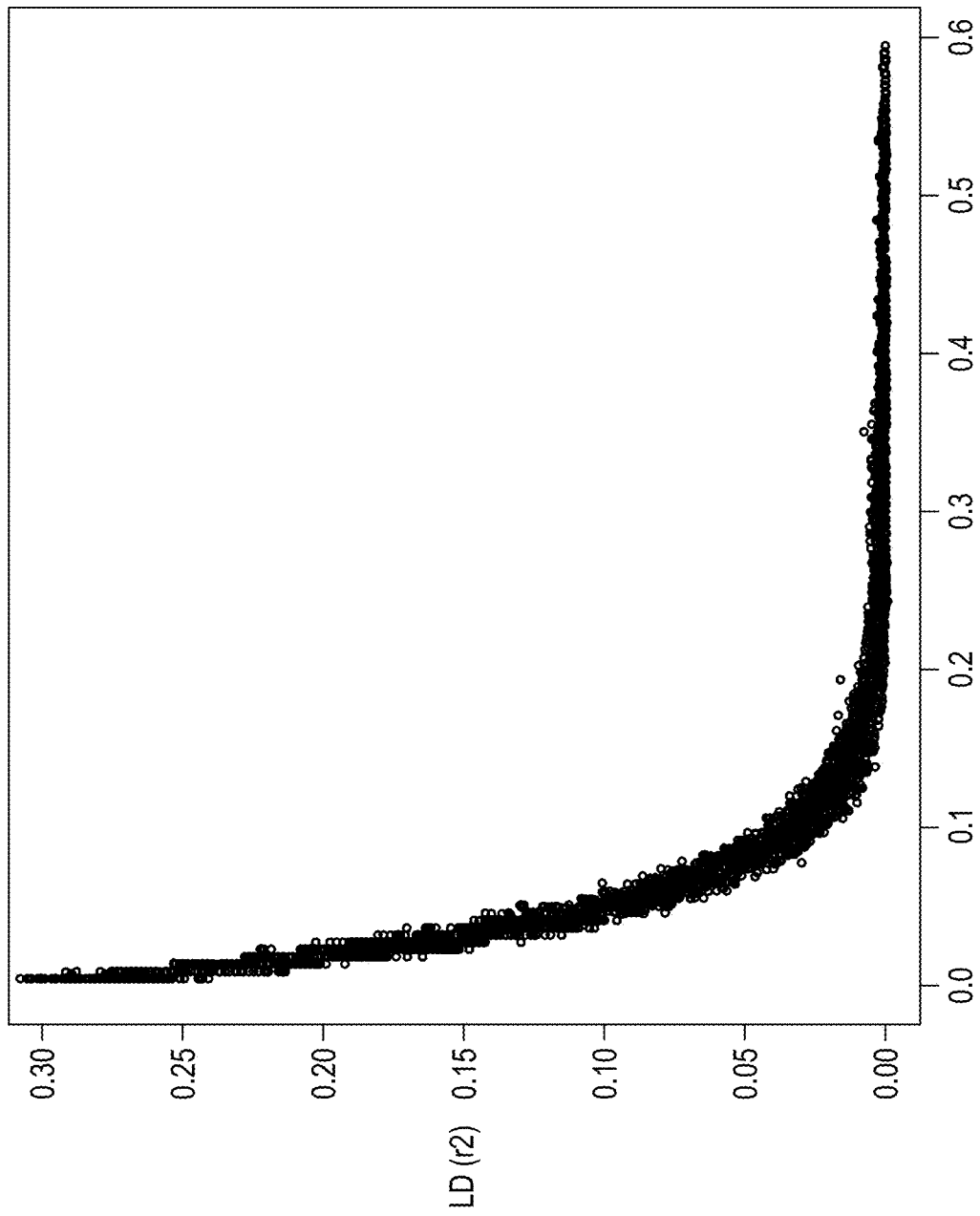

FIG. 24 shows pairwise linkage disequilibrium (LD, measured as r2) in relation to genetic distance in Morgan (M).

Figure 25:
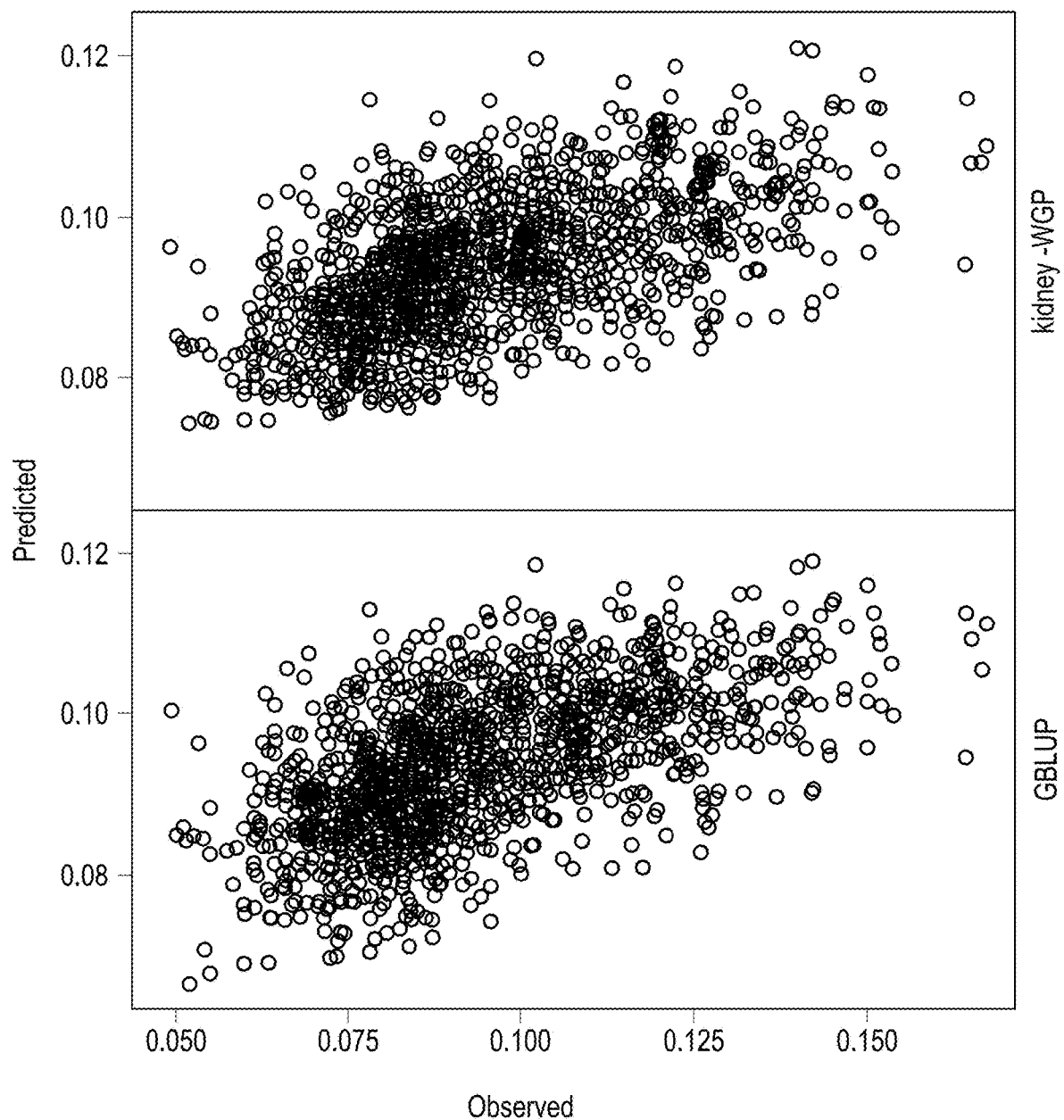

FIG. 25 shows predicted vs. observed urinary sodium excretion (UNa, mEq/l) of 1,450 individuals in test set for the biological-model based whole genome prediction method (Kidney-WGP) and the benchmark method GBLUP.

DESCRIPTION

Prior genomic prediction approaches to complex trait modeling use purely statistical based methodologies to explicitly model non-linear relationships between statistical model terms. Previous attempts to incorporate biological information into genomic prediction methods to reconstruct and predict the ultimate target complex traits from component traits modeled the component traits separately from the target complex trait and separately from the other component traits. These attempts failed to explicitly incorporate the non-linear relationships among the traits within the parameter estimation process. These attempts also failed to develop a framework to integrate the biological knowledge based model into the estimation procedure, and therefore do not allow simultaneous modeling of all traits and require the component traits to be observed. The invention provides a generalized quantitative prediction framework of arbitrarily complex traits through simultaneous modelling of the relationships between the target complex trait and the component traits whether they are observed or unobserved component traits and irrespective of the nature of the relationship between them. Component traits include, but are not limited to, physiological traits included in crop growth models, individual genes within gene networks, native and transgenic DNA polymorphisms.

When the relationships between the observed complex trait and the component traits are non-linear, numerical algorithms such as rejection sampling algorithms including approximate Bayesian computation (ABC) allow simultaneous estimation of arbitrary sets of parameters without the requirement to measure all component traits. Estimation of predictive parameters is facilitated by integrating a biological knowledge based model, explicitly mapping the relationships between the observed complex trait and the (possibly) unobserved component traits, into sampling algorithms. Examples of biological knowledge based models include physiological crop growth models, gene networks, and biochemical pathways. The predictive parameters can then be used to predict the complex trait and the component traits when either or both are unobserved.

One embodiment of the invention includes methods for enhanced genome wide prediction to select inbreds and hybrids with drought tolerance to improve crop yield under drought conditions and parity yield performance under more favorable environmental conditions. Another embodiment of the invention includes enhanced multi-trait genome wide prediction for selecting inbreds and hybrids with improved yield and agronomic performance for specific target environments. Another embodiment of the invention includes enhanced genome wide prediction for selection of inbreds and hybrids with improved yield and agronomic performance for target geographies where genotype-by-environment interactions are important. Another embodiment of the invention is enhanced genome wide prediction of the combined effects of transgenic and native genetic variation on inbred and hybrid yield and agronomic performance for each of the methods described above.

EXAMPLES

Example 1: Generic Trait Simulation

In this example, a two-trait model was simulated then modeled using approximate Bayesian computation methods and these results were compared with a genomic best linear unbiased prediction (GBLUP) method. In the two-trait model, a first trait, T1, controls if a genotype crosses a certain physiological threshold, such as the transition from the vegetative developmental phase to the reproductive developmental phase, which in turn determines whether flowering occurs before or after onset of dry weather in an water limited environment. T1 may be flowering time itself, for example, or it may be a genotype dependent parameter in a crop growth model (CGM), such as a basal temperature requirement for the developmental transition, with which flower time can be computed. A second trait, T2, is sensitive to whether the particular threshold is crossed. An example could be yield formation, which works differently in an environment when water is not limited than in an environment when water is limited because of a too late onset of the reproductive developmental phase. To symbolize this mechanism, the second trait may be designated T2+ or T2– to indicate yield formation under water unlimited and limited conditions, respectively.

To simulate this trait hierarchy, T1 was controlled by 25 SNPs, T2+ by 25 SNPs and T2– by 25 SNPs. Some of these SNPs had an effect on several of the traits, e.g., on T1 and T2+. Because of this, the average number of causative SNPs was 65. The effects of the causative SNPs $u=[u_1, u_{2+}, u_{2-}]$ for T1, T2+ and T2–, respectively, were drawn from a standard normal distribution and were always trait specific (even if the SNP had effects on multiple traits). The causative SNPs were randomly placed on a single chromosome of 3 Morgans length. In addition to the causative SNPs, which were assumed unobserved, 100 observed SNP markers were placed on the chromosome.

The simulation created 2,000 double haploid (DH) lines from a bi-parental cross, with meiosis along the chromosome simulated according the Haldane mapping function. All unobserved and observed SNPs were segregating in the cross. Phenotypes for T2, denoted as $y_2$ were computed as $$y_2 | y_1 = \begin{cases} Z_{2+}u_{2+}, & y_1 < 0 \\ Z_{2-}u_{2-}, & y_1 \geq 0 \end{cases} \quad (1)$$

where $y_1 = Z_1 u_1$ and $Z_1$, $Z_{2+}$ and $Z_{2-}$ denote the genotype matrices of the 2,000 DH at the causal SNPs for the three traits. The T1 phenotype $y_1$ was centered and 0 used as the physiologically critical threshold. From the 2,000 DH, 50 were randomly chosen as the estimation set.

Approximate Bayesian computation (ABC). The model relating marker genotypes to phenotypes corresponded to the one used to generate the DH phenotype data from the simulated causative SNPs, but only in terms of the principles embodied in equation (1). The critical threshold of 0 was taken as known as well as the fact that T1 is the trait that determines if a genotype crosses the threshold or not. It is further assumed known that T2 is physiologically sensitive to whether the threshold is crossed or not, i.e., that genetic control might be different and context dependent on whether the threshold is or is not crossed. However, ignorance was assumed on any specifics of the unobserved genetic architecture of traits T1 and T2, such as which SNPs control which trait (the causal SNPs were anyway unobserved). We thus fitted three marker effects for all 100 observed SNPs, one for T1, T2+ and T2−. The model fitted was $$y_2 | x_1 = \begin{cases} Za_{2+}, & x_1 < 0 \\ Za_{2-}, & x_1 \geq 0 \end{cases} \quad (2)$$

where $x_1 = Za_1$. Here Z was the genotype matrix of the 100 observed SNPs and $a = [a_1, a_{2+}, a_{2-}]$ was the vector of estimated marker effects. For the prior of the marker effects a we used a normal distribution with mean 0 and variance 0.05.

Sampling. The ABC rejection sampling algorithm proceeds as follows:
1. Draw a candidate a' from the prior.
2. Generate new data $y_2$' according to equation (2).
3. Compute the Euclidean distance d between the vectors $y_2$' and $y_2$.
4. If d is below a tolerance level, a' is accepted as a sample of the posterior distribution $P(a|y_2, H)$.
5. Repeat 1 to 4 for a sufficient number of samples.

The tolerance level for accepting candidates was determined in a 'initialization run' to achieve a acceptance rate of 2.5/1,000,000. 25 parallel samplers were run on a parallel computing cluster to obtain 125 draws from the posterior. The algorithm is easily scalable. So having 125 cpu's available would cut the computing time to a few minutes. $P(a|y_2, Z, H)$ is dependent only on $y_2$, Z and H, the latter of which embodies the quantitative relationships among the observed and unobserved traits that collectively represent the biological knowledge. The trait T1 or the causal SNP are unobserved and not directly used for estimation other than through their embodiment in H.

Figure 1:
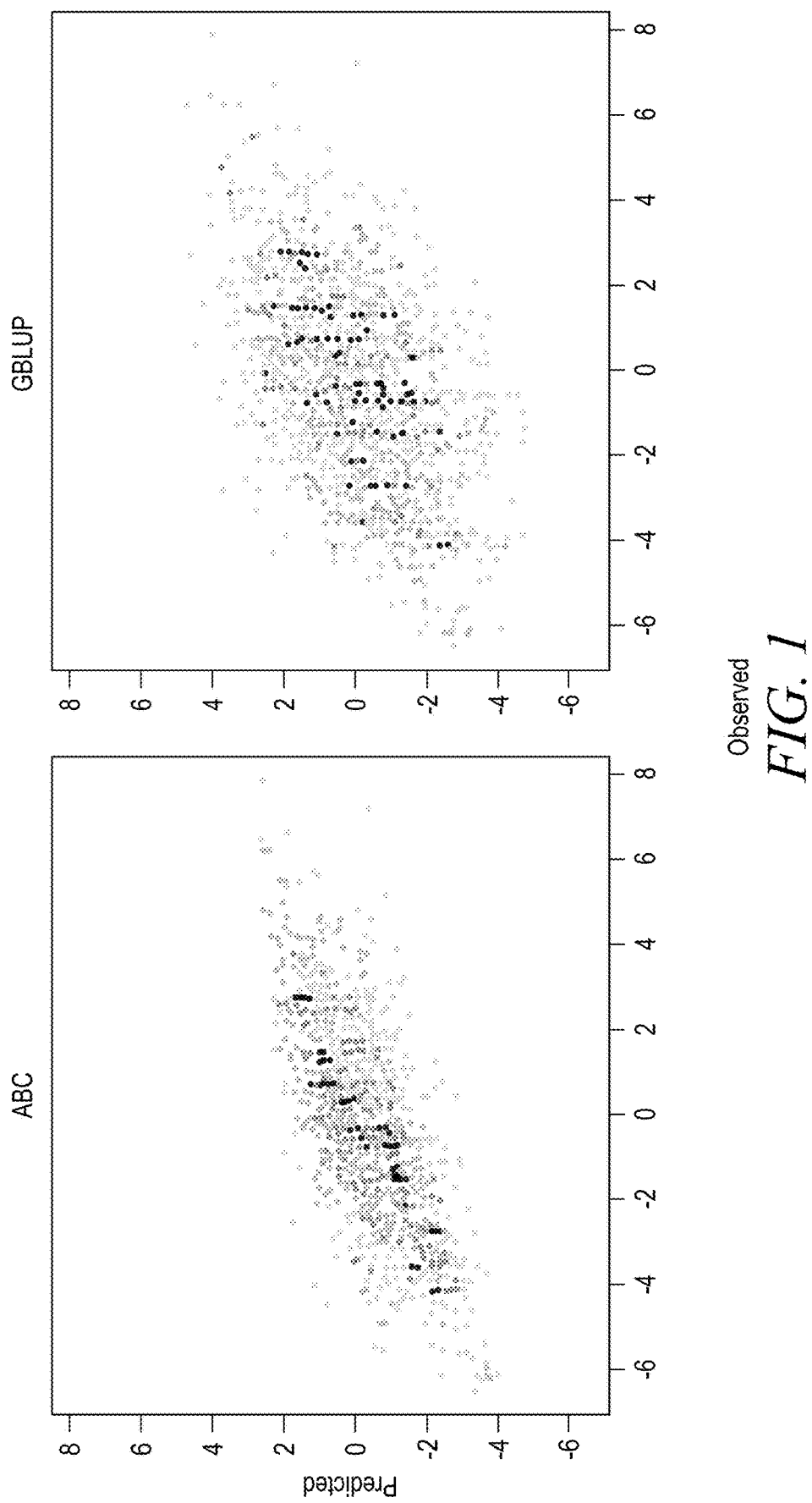
FIG. 1 is a graph of predicted vs. observed values in the validation set for ABC (correlation 0.78) and GBLUP (correlation 0.52).
Figure 2:
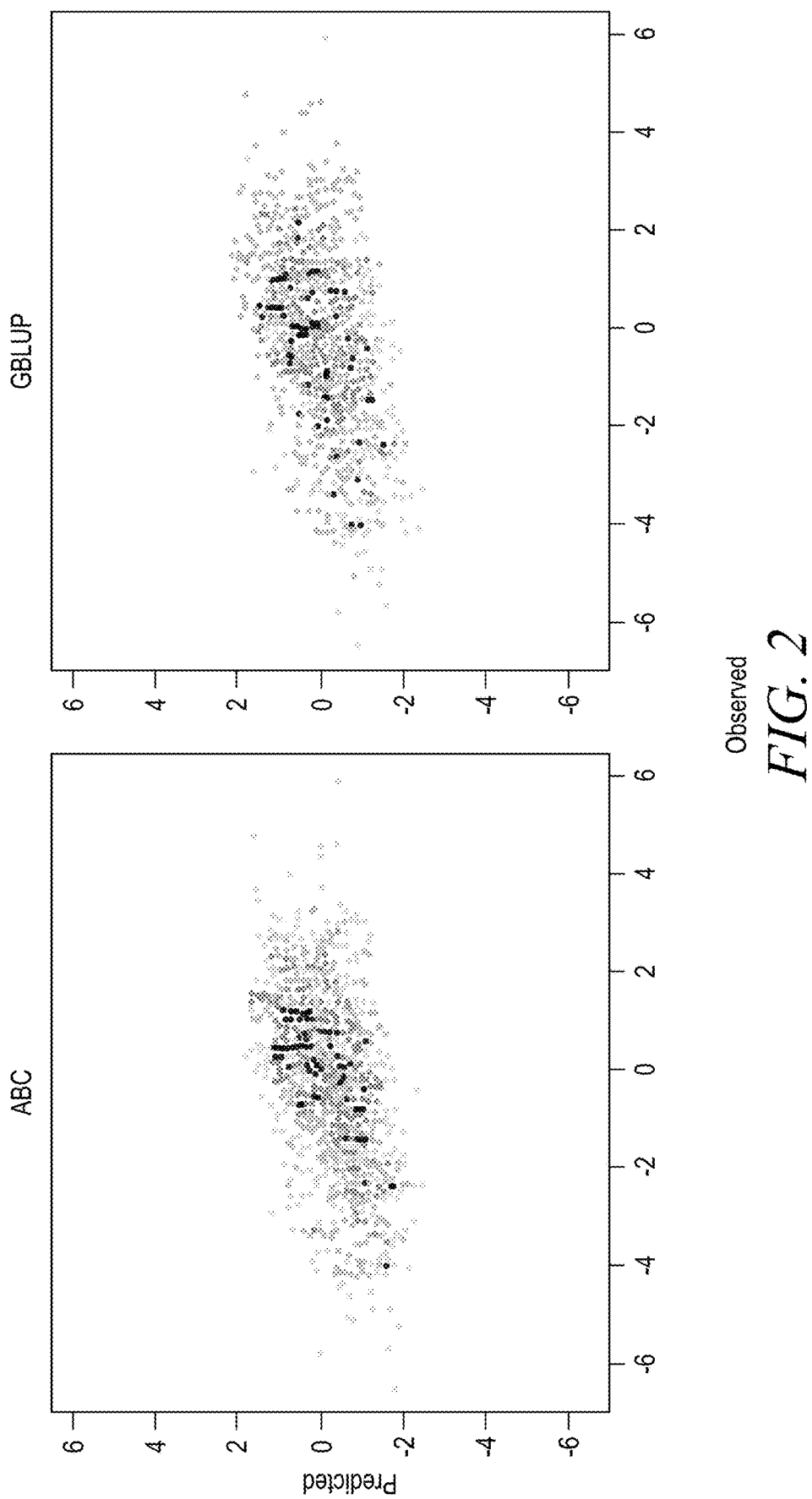
FIG. 2 is a graph of predicted vs. observed values in the validation set for ABC (correlation 0.57) and GBLUP (correlation 0.51).

As a comparison, a standard genomic BLUP model was fitted to the data. Results obtained by using the estimation set of 50 DHs were used to predict $y_2$ for the remaining 1,950 DH individuals. FIG. 1 shows one example were ABC achieved an accuracy (correlation of predicted and observed values) of 0.78 while GBLUP achieved a lower value of 0.52. The simulation was repeated several times, and ABC always achieved a higher prediction accuracy than GBLUP, albeit with smaller differences in some cases (FIG. 2).

Example 2: Incorporation of Crop Growth Model to Predict Final Biomass Yield

This example demonstrates that ABC may be used with information provided through a crop growth model. The Muchow, et al., (1990) crop growth model models corn biomass (BM) growth as a function of temperature and solar radiation as well as of several physiological traits (PTs) of the plant. All PTs could be genotype specific, meaning that marker effects should be estimated for these. As a first step, however, all PTs were set to meaningful constants and only the Total Leaf Number (TLN) was modeled as genotype specific. TLN is a key PT and factors, directly or indirectly, into most equations comprising the CGM. The non-linear relationship between TLN and final BM is shown graphically in FIG. 3.

Genotypes: TLN was simulated to be controlled by 10 causal SNPs with additive effects of similar magnitude. These causal SNPs were randomly placed on a single chromosome of 3 Morgans length and assumed to be unknown. Another 110 observed SNP markers were also placed randomly onto the chromosome. 2,000 DH lines from a bi-parental cross were generated by simulating meiosis along the chromosome according to the Haldane mapping function. All unobserved and observed SNPs were segregating in the cross. After determining the TLN of all DH, their BM values were computed according to the CGM. Of the 2,000 DH lines, 100 were used as estimation set, the remainder for validation.

ABC: The CGM that generated the phenotypic data was assumed to be known, including the values of all PT, except TLN, which was modeled as $$TLN_i = \mu_{TLN} + z_i u_{TLN} \quad (1)$$

where $\mu_{TLN}$ was the intercept, $z_i$ the genotype vector of the 110 SNP markers for DH line i and $u_{TLN}$ was the vector of marker effects. The only observed parameters were $z_i$ and the final biomass BM, henceforth denoted as y. TLN was not observed.

The ABC rejection sampling algorithm proceeded as follows:
1. Draw candidates for $\mu_{TLN}$ and $u_{TLN}$ from prior.
2. Compute predicted value TLN' according to equation (1)
3. Simulate new BM data y' from the CGM
4. Compute the Euclidean distance d between the vectors y' and y
5. If d is below a tolerance level, the candidates for $\mu_{TLN}$ and $u_{TLN}$ were accepted as samples from the posterior distribution $P(\mu_{TLN}, u_{TLN}|y, H)$.
6. Repeat 1 to 5 until a sufficient number of samples was drawn.

As with $\mu_{TLN}$ a Gaussian distribution was used with a mean equal to 9.5, which was the simulated mean of TLN, and standard deviation of 2. Thus considerable prior knowledge about $\mu_{TLN}$ was assumed to be available, which is a reasonable assumption. The prior for $u_{TLN}$ was a Gaussian distribution with mean zero and standard deviation 0.25. The tolerance was chosen such that the acceptance rate was ≈$10^{-6}$, the number of samples drawn was 200. As a benchmark, a standard GBLUP model was also fitted to the data.

Results

Figure 4:
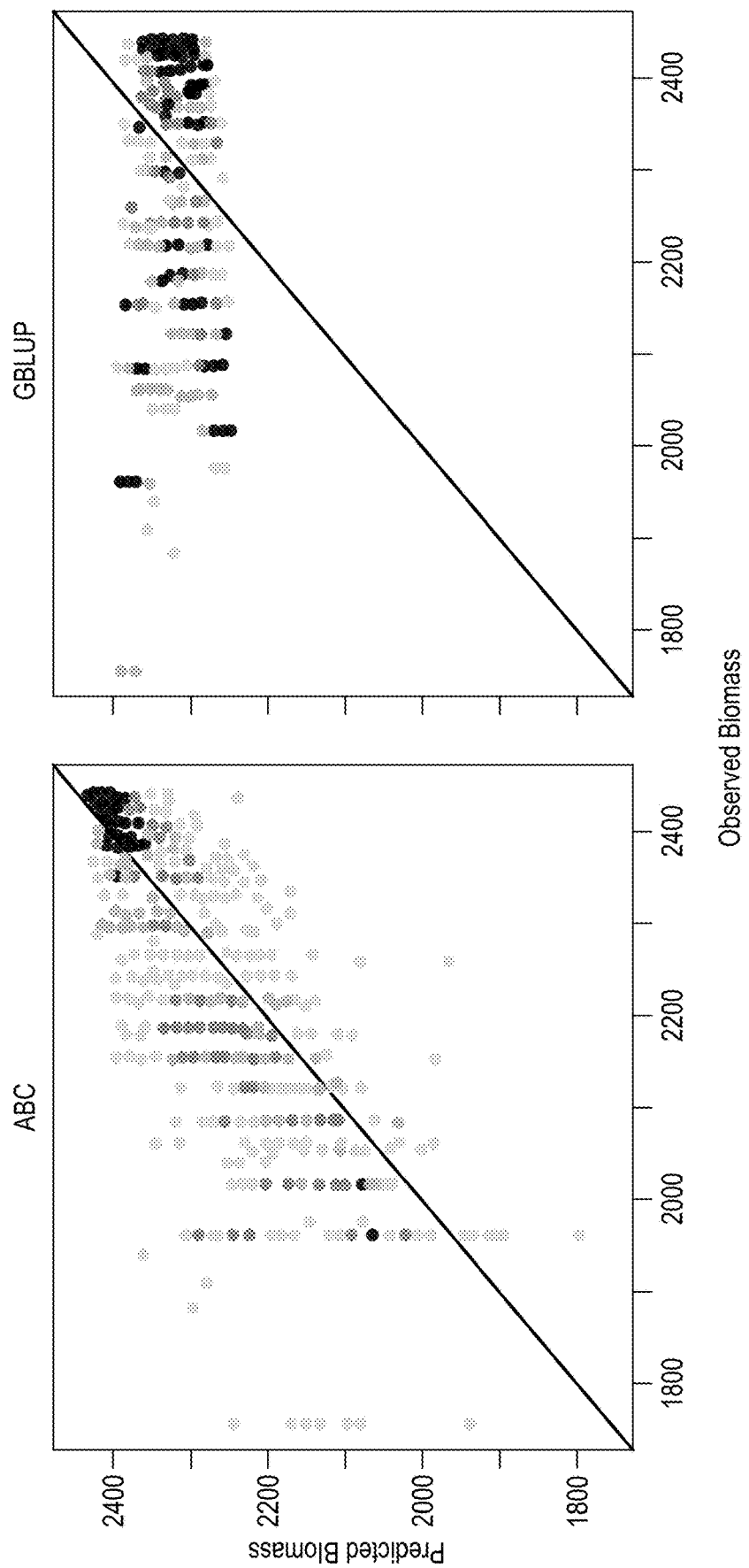
FIG. 4 is a graph of predicted vs. observed final biomass yield (BM) for ABC and GBLUP.

Predicting BM: The prediction accuracy for BM (correlation between predicted and observed values among DH lines in the validation set) achieved with ABC was always considerably higher than that achieved with GBLUP. Averaged over 10 replications of the simulation, ABC achieved an accuracy of 0.85, GBLUP only 0.15. A representative example is shown in FIG. 4.

Figure 5:
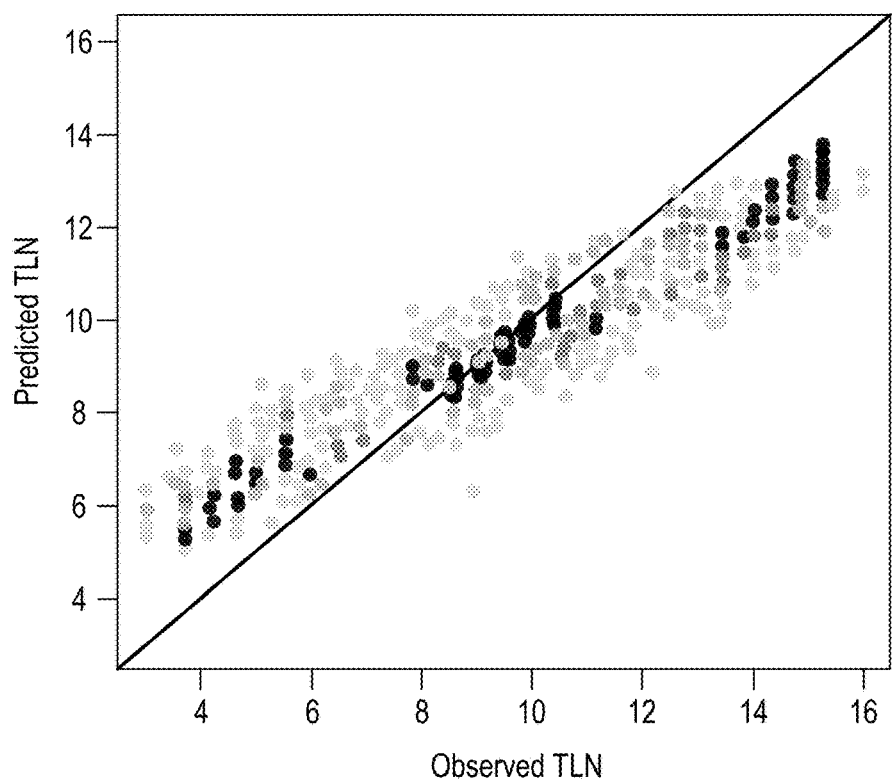
FIG. 5 is a graph of Total Leaf Number (TLN) predicted by ABC vs. "observed" TLN values of DH line in the validation set. Note that TLN was unobserved when fitting the model.

Predicting TLN: With ABC it is possible to obtain predictions for the unobserved trait TLN, based on the quantitative relationships embodied in the CGM and the formal incorporation of the CGM into the ABC algorithm. The prediction accuracy was very high, 0.95 in the validation set, on average. A representative example is shown in FIG. 5.

Even though TLN was unobserved, ABC succeeded in predicting the TLN values of the DH lines with high accuracy. Because of the non-linear relationship between TLN and BM, the former can only be deduced from the latter through the CGM. This demonstrates that ABC indeed made use of the CGM. The high accuracy with which BM was predicted shows the great potential advantage the method can have over standard linear whole genome regression methods, like GBLUP.

Figure 3:
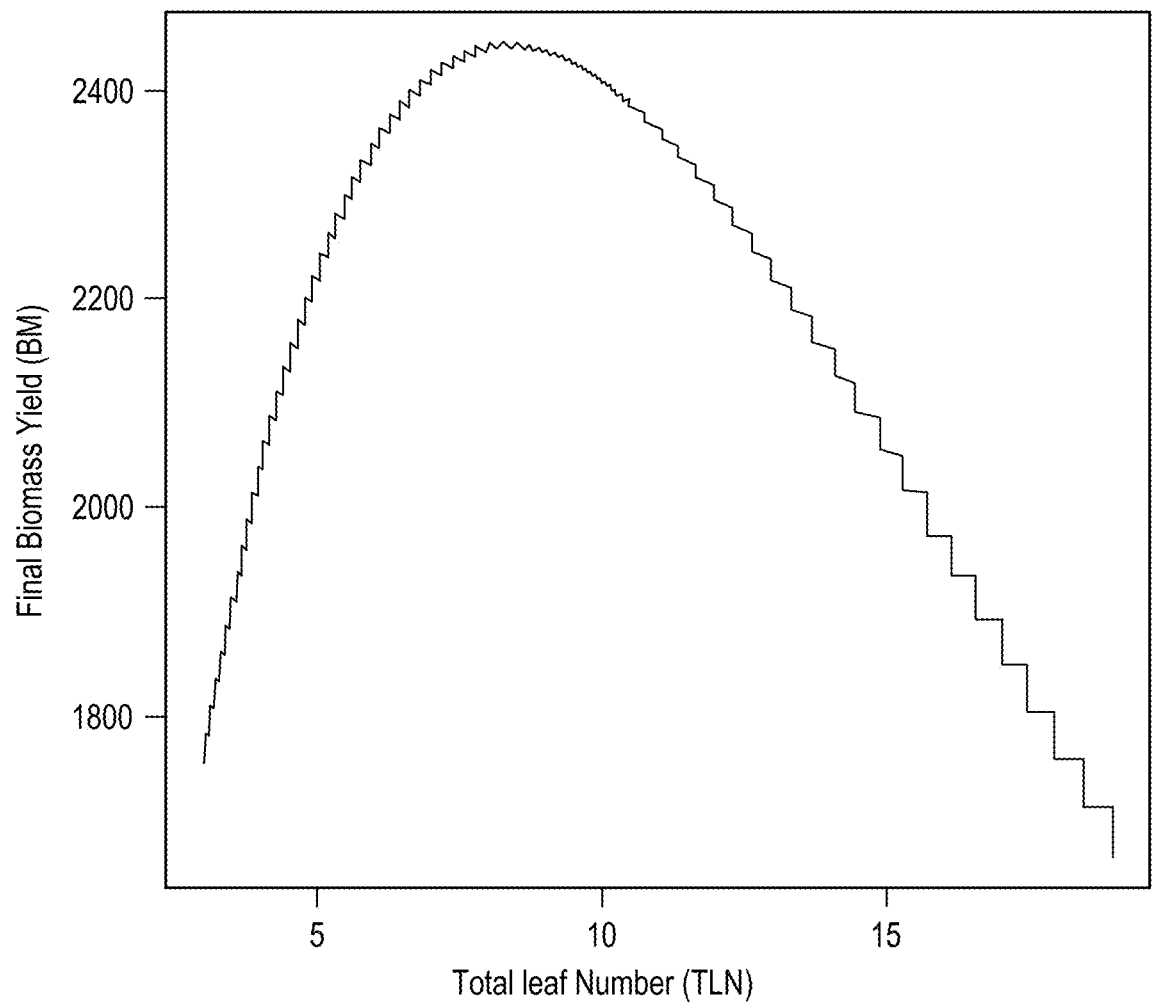
FIG. 3 is a graph of the relationship between Total Leaf Number (TLN) and final biomass yield (BM).

The effects of the causative SNPs on TLN were linear and additive. However, the relationship between TLN and BM was strongly non-linear (FIG. 3). The consequence of this is that the effects of the causative SNP on BM are non-linear as well. In essence, BM was a function of epistatic effects off all possible orders. These cannot be captured well with a linear model that directly relates BM and the marker genotypes. Hence, the very low prediction accuracy of GBLUP.

An alternative to fitting a very complex epistatic model is to break down the complex trait BM into simpler physiological traits (PT) such as TLN, which are more likely to have a simple, additive genetic architecture. Because the PT are generally not observed, model parameters can only be estimated through the relation between the PT and the observed trait (OT, BM in this example). However, in this case, the likelihood of the OT given the model parameters is unknown or does not even exist. In this situation, ABC allows sampling from the approximate posterior distribution of the parameters, using the algorithm detailed above. What ABC requires is a mechanism to simulate data given the parameters. The CGM provides this mechanism.

Example 3: Predicting Performance in New Environments

Figure 6:
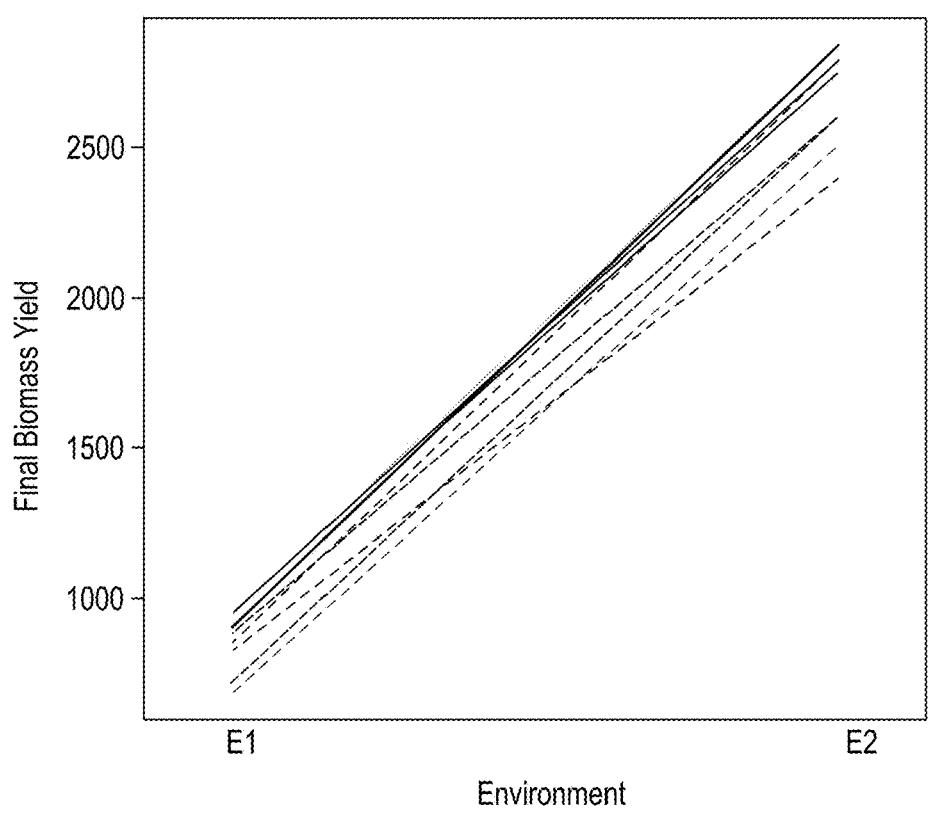
FIG. 6 is an interaction plot for biomass yield of 25 representative genotypes in environments E1 (drought) and E2 (non-drought).

Two different environments were simulated by modifying the daily solar radiation, temperature and plant population (plants $m^{-2}$). Environment 1 (E1) had a plant population of 2, a daily temperature of 28° C. and a daily solar radiation of 36 MJ $m^{-2}$. Environment 2 (E2) had a plant population of 10, a daily temperature of 18° C. and a daily solar radiation of 20 MJ $m^{-2}$. Thus, E1 was an extremely dry and heat stressed environment in which only a very low plant density can be used because of water limitations. In contrast E2 was more favorable for plant growth with low likelihood of water limitations or heat stress and higher plant density could be used. The CGM used here can generate cross-over genotype by environment by management (G×E×M) interactions between E1 and E2, with a rank correlation of only 0.62 (FIG. 6).

To test if the ABC rejection sampling algorithm could be used to predict performance in new environments, the E2 phenotypic data from a random subset of 100 DH lines was used for estimation of marker effects and then the performance of the remaining 1,900 DH lines was predicted in E1 and E2, as described above. The average prediction accuracy (over 10 replications) for performance in E1 and E2 was 0.87 (FIG. 7). Thus, performance in new environments can be predicted, as long as the PT traits can be predicted and the relationships within the CGM apply to the new environment.

GBLUP was used as a benchmark again. Because it cannot account for the different environmental conditions in E1 and E2, the predicted value is the same for both. GBLUP achieved an average accuracy of 0.36 for prediction in E2. In the new environment E1, however, the accuracy was −0.27, likely because of the cross-over interaction, which cannot be accounted for (FIG. 8).

Two Genotype Specific Traits: Previously, only TLN was assumed to be genotype specific. Now, the PT 'area of largest leaf' (AM), which influences average leaf size, was simulated to be genotype specific, too. AM was simulated as described for TLN above and linearly interpolated to a range between 450-650 $cm^2$. AM was modeled as $AM_i=\mu_{AM}+z_i+u_{AM}$, and the ABC rejection sampling algorithm explained above was extended to allow for estimating of two vectors of parameters, (for TLN and AM).

Example 4: Increased Complexity Crop Growth Model to Predict Final Biomass Yield The Muchow, et al., (1990) crop growth model (CGM) models corn biomass (BM) growth as a function of plant population (plant density), temperature and solar radiation as well as of several physiological traits (PT) of the plant. The PT were Total Leaf Number (TLN), Area of Largest Leaf (AM), Solar Radiation Use Efficiency (SR) and Thermal Units to Physiological Maturity (MTU). SR was set to a constant value of 1.6 g $MJ^{-1}$ and MTU to 1150, the values used by Muchow, et al., (1990). TLN and AM were simulated to be genotype specific, as described below.

Two different environments were simulated by modifying the daily solar radiation, temperature and plant population (plants $m^{-2}$). Environment 1 (E1) had a plant population of 2, a daily temperature of 28° C. and a daily solar radiation of 36 MJ $m^{-2}$. Environment 2 (E2) had a plant population of 10, a daily temperature of 18° C. and a daily solar radiation of 20 MJ $m^{-2}$. Thus, E1 is considered as an extremely dry and heat stressed environment in which only a very low plant density can be used because of water limitations. In contrast E2 is considered more favorable for plant growth with low likelihood of water limitations or heat stress and higher plant density could be used. Plant population is considered an agronomic management (M) component of the environment. Therefore, the CGM used here could generate cross-over genotype by environment by management (G×E×M) interactions between E1 and E2, with a correlation of 0.69 (FIG. 8). Only phenotypic data from E2 was used for estimation.

Data simulation: TLN and AM were controlled by separate sets of 10 causal SNP with additive effects of similar magnitude. These causal SNP were randomly placed on a single chromosome of 3 Morgans length and assumed to be unknown. Another 100 observed SNP markers were also placed randomly onto the chromosome. 2,000 DH lines from a bi-parental cross were generated by simulating meiosis along the chromosome according the Haldane mapping function. All unobserved and observed SNP were segregating in the cross. A linear interpolation was applied to the initially obtained TLN and AM values, such that TLN had a range of [3,16] with a mean of 9.5 and AM a range of [500,600] with a mean of 550.

After determining TLN and AM of all DH lines, their BM values for environments E1 and E2 were computed according to the CGM. Of the 2,000 DH lines, 100 were used as an estimation set, the remainder for validation. To simulate residual variation, we added a normally distributed noise variable to the BM values of the estimation set lines in E2, which were used for fitting the model. The variance of the noise variable was chosen such that heritability ($h^2$)=0.85. Ten independent data sets were obtained by replicating the whole simulation.

ABC-CGM: The CGM that generated the data was assumed to be known, including the values of all PT, except TLN and AM, which were modeled as:

$$TLN_i = \mu_{TLN} + z_i u_{TLN} \quad (1)$$

$$AM_i = \mu_{AM} + z_i u_{AM} \quad (2)$$

where $\mu_{TLN}$ and $\mu_{AM}$ were intercepts, $z_i$ the genotype vector of the 100 SNP markers for DH line i and $u_{TLN}$ and $u_{AM}$ were the vectors of marker effects. The only observed properties were $z_i$ and the final biomass BM, henceforth denoted as y. TLN and AM were not observed.

To accommodate the presence of environmental noise within the estimation data set that is not explained by the CGM, the following likelihood function was used as a model of the data:

$$y_i \sim N(CGM_i, \sigma). \quad (3)$$

Thus, a Gaussian distribution was used with mean equal to the BM yield value obtained from the CGM and a standard deviation σ, which depends on $h^2$ and was assumed to be known. Note that because (3) is a known likelihood function, the use of ABC would not strictly be required and could be replaced by more conventional rejection samplers.

The ABC rejection sampling algorithm proceeded as follows:
1. Draw candidates for $\mu_{TLN}$, $\mu_{AM}$, $u_{TLN}$ and $u_{AM}$ from their priors.
2. Compute predicted values of TLN' and AM' according to equations (1) and (2)
3. Use the CGM to compute $CGM_i$
4. Simulate new BM data y' from (3)
5. Compute the Euclidean distance d between the vectors y' and y
6. If d is below a tolerance level, the candidates for $\mu_{TLN}$, $\mu_{AM}$, $u_{TLN}$ and $u_{AM}$ were accepted as samples from the posterior distribution $P(\mu_{TLN}, \mu_{AM}, u_{TLN}$ and $u_{AM}|y, H)$.
7. Repeat 1 to 6 until a sufficient number of samples was drawn.

As prior for $\mu_{TLN}$ and $\mu_{AM}$ we used Gaussian distributions with means equal to 9.5 and 550, respectively, and standard deviations of 2.5 and 50, respectively. Considerable prior knowledge about $u_{TLN}$ and $\mu_{AM}$ was assumed to be available, which is a reasonable assumption. The prior for $u_{TLN}$ was a Gaussian distribution with a mean of zero and a standard deviation of 0.5. The prior for $u_{AM}$ was a Gaussian distribution with a mean of zero and a standard deviation of 5. The tolerance was chosen such that the acceptance rate was $5 \cdot 10^{-7}$, the number of samples drawn was 200. As a benchmark, we fitted a standard GBLUP model to the data.

Results

Increased Complexity: With increased complexity, ABC-CGM was able to retain a predictive advantage over the linear method GBLUP. However, compared to the previously investigated scenario, where there was only a single varying PT with a strongly non-linear relationship to BM, the linear method GBLUP achieved a mostly decent accuracy, too. One possible explanation is that the non-linear relationships of individual PT with BM are 'masked' by the combined action of several PT. The number of varying PT and their value range influence the degree in which non-linear relationships are masked. FIG. 13 shows observed vs. fitted values from the simple linear regression model BM~TLN+AM, for increasingly narrow ranges of AM. When AM is allowed to vary between the wider range 350 and 750 $cm^2$, this simple linear model provides a reasonable fit to the data, even when there are underlying non-linear linear relationships among the PT. However, when the range of AM is reduced to [500, 600] (as in this study) or if AM is virtually fixed (as in example 2), the decidedly non-linear relationship between TLN and BM is revealed.

In addition to the masking of non-linear relationships, it should be expected that the more PT have to be accounted for, the less accurate the prediction for each one will be.

Environmental Noise: ABC-CGM could accommodate the presence of environmental noise and still achieved a higher accuracy than GBLUP.

Example 5: Three Underlying Physiological Traits

In this example, three physiological traits are simulated as genotype specific and incorporated into the estimation procedure. In this scenario with further increased complexity, ABC-CGM still outperforms conventional linear methods and can still account for genotype-by-environment interactions.

Crop growth model: The crop growth model (CGM) developed by Muchow, et al., (1990) was used. This CGM models corn biomass (BM) growth as a function of plant population (plant density), temperature and solar radiation as well as of several physiological traits (PTs) of the plant. The PTs were Total Leaf Number (TLN), Area of Largest Leaf (AM), Solar Radiation Use Efficiency (SRE) and Thermal Units to Physiological Maturity (MTU). MTU was set to 1150, the value used by Muchow et al. (1990). TLN, AM and SRE were simulated to be genotype specific, as described below.

Two different environments were simulated by modifying the daily solar radiation, temperature and plant population (plants $m^{-2}$). Environment 1 (E1) had a plant population of 10, a daily temperature of 18° C. and a daily solar radiation of 20 MJ $m^{-2}$. Environment 2 (E2) had a plant population of 2, a daily temperature of 28° C. and a daily solar radiation of 36 MJ $m^{-2}$. Thus, E2 is an extremely dry and heat stressed environment in which only a very low plant density can be used because of water limitations. In contrast E1 is considered more favorable for plant growth with low likelihood of water limitations or heat stress and a higher plant density could be used. The CGM used here could generate cross-over genotype by environment by management (G×E×M) interactions between E1 and E2 (see, FIG. 9 for an example). Only phenotypic data from E1 was used for estimation.

Data simulation: TLN, AM and SRE were controlled by separate sets of 10 causal SNPs with additive effects of similar magnitude. These causal SNP were randomly placed on a single chromosome of 1.5 Morgans length and assumed to be unknown. Another 100 observed SNP markers were also placed randomly onto the chromosome.

1,000 DH lines from a bi-parental cross were generated by simulating meiosis along the chromosome according the Haldane mapping function. All unobserved and observed SNP were segregating in the cross. A linear interpolation was applied to the initially obtained TLN and AM values, such that TLN had a range of [3,16] with a mean of 9.5, AM a range of [500,600] with a mean of 550 and SRE a range of [1.55,1.65] with a mean of 1.60.

After determining TLN, AM and SRE of all DH lines, their BM values for environments E1 and E2 were computed according to the CGM. Of the 1,000 DH lines, 200 were used as an estimation set, the remainder for validation. To simulate residual variation, a normally distributed noise variable was added to the BM values of the estimation set lines in E2, which were used for fitting the model. The variance of the noise variable was chosen such that $h^2=0.85$. Twenty independent data sets were obtained by replicating the whole simulation. The relationship between BM in E1 and TLN, AM and SRE, respectively, is shown in FIG. 14.

ABC-CGM: We assumed that the CGM that generated the data was known, however, the PT (besides MTU) were not and modeled as $$TLN_i = \mu_{TLN} + z_i u_{TLN} \quad (1)$$

$$AM_i = \mu_{AM} + z_i u_{AM} \quad (2)$$

$$SRE_i = \mu_{SRE} + z_i u_{SRE} \quad (3)$$

where $\mu_{TLN}$, $\mu_{AM}$ and $\mu_{SRE}$ were intercepts, $z_i$ the genotype vector of the 100 SNP markers for DH line i and $u_{TLN}$, $u_{AM}$ and $u_{SRE}$ were the vectors of marker effects. Observed were only $z_i$ and the final biomass BM, henceforth denoted as y. TLN, AM and SRE were not observed.

To accommodate the presence of environmental noise within the estimation data set that is not explained by the CGM, the following likelihood function was used as a model of the data $$y_i \sim N(CGM_i, \sigma). \quad (4)$$

Thus, a Gaussian distribution was used with mean equal to the BM yield value obtained from the CGM and a standard deviation σ, which depends on $h^2$ and was assumed to be known.

The ABC rejection sampling algorithm proceeded as follows:
1. Draw candidates for $\mu_{TLN}$, $\mu_{AM}$, $\mu_{SRE}$, $u_{TLN}$, $u_{AM}$ and $u_{SRE}$ from their priors.
2. Compute predicted values of TLN', AM' and SRE' according to equations (1-3)
3. Use the CGM to compute $CGM_i$
4. Simulate new BM data y' from equation (4)
5. Compute the Euclidean distance d between the vectors y' and y
6. If d is below a tolerance level τ, the candidates for $\mu_{TLN}$, $\mu_{AM}$, $\mu_{SRE}$, $u_{TLN}$, $u_{AM}$ and $u_{SRE}$ were accepted as samples from the posterior distribution P(parameters|y, H).
7. Repeat 1 to 6 until a sufficient number of samples was drawn.

As prior for $\mu_{TLN}$, $\mu_{AM}$ and $\mu_{SRE}$ we used Gaussian distributions with a means equal to 9.5, 550 and 1.6, respectively and standard deviations of 0.75, 25 and 0.1, respectively. This assumes that considerable prior knowledge about $\mu_{TLN}$, $\mu_{AM}$ and $\mu_{SRE}$ was available, which is typically the case.

The prior for the effect of the $j^{th}$ marker on trait X was $u_{X_j} \sim N(0, \sigma_X)$ The parameter $\sigma_x$ was computed as $\sigma_x = \sqrt{var(X)/M}$ where M was the number of markers, var(X) was the phenotypic variance of trait X, which was assumed to be known. The tolerance τ was chosen such that the acceptance rate was $2 \cdot 10^{-6}$, the number of samples drawn was 100. As a benchmark, we fitted a standard GBLUP model to the data.

Results

Conventional linear method GBLUP. GBLUP models were fitted to the same 20 data sets to obtain benchmark results. GBLUP achieved an average prediction accuracy for BM of 0.51 and 0.05, for E1 and E2, respectively. The prediction accuracy of the PT traits was −0.49, 0.19 and 0.42 for TLN, AM and SRE, respectively.

ABC-CGM. The average prediction accuracy for physiological traits TLN, AM and SRE in the validation set was 0.85, 0.28 and 0.44, respectively (FIG. 15). The average prediction accuracy for final biomass yield BM was 0.80 in E1 and 0.70 in E2 (FIG. 16).

Superiority of ABC-CGM. The effects of the causative SNPs on the physiological traits TLN, AM and SRE were linear and additive. However, the relationship between these traits and BM was non-linear, especially between TLN and BM (FIG. 14). The consequence of this is that the effects of these causative SNPs on BM are non-linear as well. BM was a function of epistatic effects off all possible orders. These cannot be captured well with a linear model that directly relates BM and the marker genotypes. Hence, the lower prediction accuracy of GBLUP, even in environment E1, the same environment where the estimation data came from.

ABC-CGM models the functional relationship between biomass yield and underlying physiological traits and incorporates environment specific weather and management information (solar radiation, temperature and planting density). This enables ABC-CGM to predict even cross-over G×E×M interactions and to deliver high prediction accuracy even in fundamentally different environments. Conventional linear methods like GBLUP do not explicitly model the non-linear relationships among the traits or the G×E×M interactions and are therefore oblivious to characteristics of specific environments and how they determine crop growth. They therefore fail to predict performance across environments under strong G×E×M.

Causal inference. Because ABC-CGM models functional relationships, it can also provide insides into physiological and genetic determinants of G×E×M. The lower the importance of a parameter in a complex system (e.g., of a physiological trait in the CGM), the higher the posterior uncertainty about it, because the less the posterior of the parameter is informed and constrained by the data. If a parameter has no role for determining BM at all in an environment, its posterior uncertainty should be equal to the prior uncertainty. The posterior uncertainty can therefore be used as an indicator of the relative importance of physiological traits for driving performance in target environments. Thus, in this example, the most important trait for determining BM performance in E1 was TLN, followed by AM and then SRE (FIG. 17).

Example 6: Prior Distributions and Sampling Parameters

In this example the effect of prior distributions and ABC sampling parameters on prediction accuracy were investigated. The data simulation and crop growth model were identical to example 3.

Prior definitions for marker effects: The prior for the effect of the $j^{th}$ marker on trait X was $$u_{X_j} \begin{cases} \sim N(0, \sigma_X) & \text{with probability } (1-\pi) \\ = 0 & \text{with probability } \pi \end{cases} \quad (5)$$

The parameter $\sigma_x$ was computed as $$\sigma_x = \sqrt{\frac{s \cdot \text{var}(X)}{(1-\pi)M}}$$

where M was the number of markers, var(X) was the phenotypic variance of trait X, which was assumed to be known, and s was a scaling factor which was used to simulate prior misspecification. As values for s we considered 1.0, 2.0, 0.1 and 10.0.

For the prior model inclusion probability $(1-\pi)$ values equal to 1.0, 0.9, 0.7, 0.5, 0.3 and 0.1 were considered. For $(1-\pi)<1.0$, the prior (5) corresponds to the BayesC $\pi$ prior, whereas for $(1-\pi)=1.0$ it corresponds to BayesC.

Sampling parameters: Decreasing the tolerance $\tau$ decreases the degree of approximation of the posterior which should lead to more accurate predictions. However, this is associated with an increase in computation time because decreasing requires decreasing the acceptance rate $\rho$. In practice, $\tau$ is determined by setting a target value for $\rho$ that is computationally feasible. In this study we used values for $\rho$ equal to $10^{-4}$, $10^{-5}$, $2 \cdot 10^{-6}$, $10^{-6}$ and $10^{-7}$.

Increasing the number of samples T drawn from the posterior distribution is also expected to increase prediction accuracy because quantities like the posterior means or quantiles can be estimated more accurately. However, increasing the number of samples T also increases computation time. Here we used values for T equal to 25, 50, 100, 150, 200 and 500.

A step-wise approach was used in which only one factor was investigated at a time with all the others fixed at reasonable values or at values found to be optimal in previous steps. The following sequence was used:
1. s was varied, while keeping $(1-\pi)=1.0$ with $\rho=2 \cdot 10^{-6}$ and T=100
2. $\rho$ was varied, while keeping s constant at 1.0, $(1-\pi)=1.0$ and T=100
3. T was varied, while keeping s constant at 1.0, $(1-\pi)=1.0$ and $\rho=2 \cdot 10^{-6}$
4. $(1-\pi)$ was varied, while keeping s constant at 1.0, T=100 and $\rho=2 \cdot 10^{-6}$ Results Varying s: The prediction accuracy for BM in both environments and for TLN, AM and SRE was highest when the variance scaling factor was equal to 1.0 (Table 1). Accuracies decreased for scaling factors below or above 1.0.

TABLE 1

Average prediction accuracies for different prior variance scaling factors s

| s | BM (E2) | BM (E1) | TLN | AM | SRE |
|---|---|---|---|---|---|
| 0.1 | 0.68 | 0.46 | 0.63 | 0.15 | 0.34 |
| 1.0 | 0.80 | 0.70 | 0.85 | 0.28 | 0.44 |
| 2.0 | 0.75 | 0.58 | 0.64 | 0.19 | 0.40 |
| 10.0 | 0.30 | 0.03 | 0.28 | 0.10 | 0.37 |

Varying $\pi$: Prediction accuracies for all traits decreased strongly with increasing $\pi$. It is possible that much higher samples sizes T would be required to accurately estimate the marker effects when they are not equal to zero.

Varying T: Prediction accuracies for BM in both environments reached a maximum at T=100 (Table 2). The prediction accuracies for TLN, AM and SRE tended to increase with increasing T too. The large fluctuations between the levels of T for the PT, however, were within the standard errors (details not shown).

TABLE 2

Average prediction accuracies for different sample sizes T

| T | BM (E2) | BM (E1) | TLN | AM | SRE |
|---|---|---|---|---|---|
| 25 | 0.78 | 0.66 | 0.74 | 0.21 | 0.36 |
| 50 | 0.79 | 0.68 | 0.80 | 0.15 | 0.35 |
| 100 | 0.80 | 0.70 | 0.85 | 0.28 | 0.44 |
| 150 | 0.80 | 0.70 | 0.76 | 0.25 | 0.40 |
| 200 | 0.80 | 0.70 | 0.76 | 0.32 | 0.41 |
| 500 | 0.80 | 0.69 | 0.77 | 0.29 | 0.48 |

Varying $\rho$: Prediction accuracies for BM in both environments increased with decreasing acceptance rate $\rho$. However, good accuracies were already observed at intermediate acceptance rates of 2 in a million, for which computations are feasible with reasonable effort. Prediction accuracies for the physiological traits increased as well. They seemed to peak at an acceptance rate of 1/1,000,000 and fluctuated afterwards. These fluctuations, however, were well within the standard error (not shown).

TABLE 3

Average prediction accuracies for different acceptance rates rho $\rho$ (in accepted samples per million). Column tau shows the average value of tolerance $\tau$ (expressed as root mean squared difference).

| rho | BM (E2) | BM (E1) | TLN | AM | SRE | tau |
|---|---|---|---|---|---|---|
| 0.1 | 0.82 | 0.73 | 0.81 | 0.27 | 0.43 | 117 |
| 1 | 0.80 | 0.71 | 0.84 | 0.27 | 0.50 | 123 |
| 2 | 0.80 | 0.70 | 0.85 | 0.28 | 0.44 | 125 |
| 10 | 0.78 | 0.66 | 0.68 | 0.23 | 0.40 | 129 |
| 100 | 0.74 | 0.58 | 0.58 | 0.22 | 0.34 | 138 |

Example 7: Application of CGM-WGP to Multi-Environment Trials

CGM-WGP methodology was applied to an empirical maize drought multi-environment trial (MET) data set to evaluate the steps involved in reduction to practice. Positive prediction accuracy was achieved for hybrid grain yield in two drought environments for a sample of doubled haploids from a cross. This was achieved by including variation for five traits into the CGM to enable the CGM-WGP methodology. The five traits were a priori considered to be important for yield variation among the maize hybrids in the target drought environments.

The MET data set selected to evaluate the empirical implementation of the CGM-WGP method was based on grain yield results obtained for a single biparental cross tested in two drought environments (treatments) at a single location. The parents of the biparental cross were selected to contrast for their grain yield breeding value under drought; one parent previously characterized to have high breeding value and the other low breeding value. The parents were crossed to produce the F1 generation and the F1 self-pollinated to produce the F2 generation. The biparental cross was represented by 106 Doubled Haploid (DH) lines derived from a random sample of individuals from the F2 generation. The 106 DH lines were genotyped with a total of 86 single nucleotide polymorphic (SNP) markers distributed across the 10 chromosomes. The SNPs were previously identified to be polymorphic between the two parents. The 106 DH lines were crossed with an inbred tester line to generate testcross hybrid seed. The tester line was selected from the complementary heterotic group and was considered to have high breeding value for grain yield under drought. All grain yield data were generated on the testcross hybrid seed for the 106 DH lines.

The 106 DH lines were evaluated for grain yield in experimental plots in two drought environments. The two drought environments were generated by creating two drought treatments in two experiments conducted in adjacent fields. Quantity and timing of irrigation was used to generate the different drought treatments. Irrigation was managed through a drip tape system installed in the experimental plots at planting. The experimental plots were each two rows, 4.5 m long with 0.75 m spacing between rows. The drip tape was inserted into the soil at planting beside each row in each plot of the experiment. The drought treatments were implemented by regulating the amount of irrigation water that was supplied to the plots through the drip tape system installed within the experiment. The supply of water was managed differently between the two drought experiments to generate two different levels of water supply, thus two different drought treatments. The irrigation schedule was managed to coincide the timing of the maximum water deficit with the flowering period of the 106 DH lines. A characterization of the temporal patterns of water deficit that was achieved in the two drought treatments is shown in FIG. 1.

The experimental design for both environments was based on two replicates. The 106 DH lines were evaluated in a row-column configuration together with a number of other DH lines and a set of commercial hybrid checks. For the objectives of this paper these additional DH lines and the commercial hybrid checks will not be considered further, other than to recognize that they were part of the data set from which the 106 DH lines were obtained. The grain yield data were obtained using a two-plot combine harvest system that measured the weight of grain obtained from the plot and the grain moisture content. The grain harvest weight per plot was adjusted to grain yield per unit area at 15% moisture content. The grain yield data were analyzed using a mixed model that included terms for the row and column position of the plots and the spatial correlation of the estimated plot residuals. The 106 DH lines were considered to represent a random sample of the possible DHs that could have been obtained from the biparental cross. Accordingly the genotypic term for the trait variation among the 106 DH lines was treated as random and Best Linear Unbiased Predictions (BLUPs) were obtained for grain yield of each of the 106 DH lines for both of the drought treatments.

Crop Growth Model

The CGM used in this study was based on the mechanistic model developed by Muchow et al (1990). The CGM uses concepts of resource use, resource use efficiency and resource allocation to grain to simulate yield. Light interception is modeled based on leaf appearance rate, the size of the largest leaf (AM), total node number (TLN), planting density and a coefficient of extinction. Simulation of daily increase in total mass results from the product of light interception and radiation use efficiency on a given day. Yield is simulated from the daily increase in harvest index starting three days after end of the flag leaf expansion and ending at physiological maturity.

Since the motivation of this study was to demonstrate the CGM-GWP methodology for maize populations evaluated under drought stress conditions the model was modified to simulate soil water balance, transpiration and growth response to water deficit. The soil water balance was modeled using a multilayer approach as described by Ritchie (1999). The components of the soil water balance, infiltration, runoff and evaporation were simulated as described by Muchow and Sinclair (1991). Evaporation was modeled using a two stage model. Transpiration was modeled based on mass growth and a transpiration coefficient equal to 9 Pa. The limited transpiration trait was implemented as described by Messina et al. (in press) with the difference that in this study the transpiration response to vapor pressure deficit (VPD) above a VPD breakpoint (VPDB) was modeled as a continuous linear function rather than a constant maximum value. Root water uptake was simulated using first order kinetics with the exponent of the function describing root occupancy and hydraulic conductivity; this parameter was set to 0.08. The sum of the potential water uptake across soil layers determined the soil water supply, while the transpiration calculation determined the water demand term. The ratio of these two components defined a stress index that was utilized to affect mass growth and leaf expansion.

Because the objective of the model was to simulate maize yield subject to water deficit at flowering time (FIG. 1) and the harvest index approach was inadequate to simulate maize yields in these types of stress environments, the model was modified to incorporate elements important to describe the dynamics of silk emergence and ear growth, processes which are sensitive to water deficit. The attainable harvest index was modeled as a function of a potential harvest index, which corresponds to that attained in the absence of water deficit, a potential number of silks that results from the maximum number of rows and rings in the ear, the exerted number of silks three days after silking, and the potential increase in kernel weight when the source exceeds the sink capacity. Kernel weight can increase about 20% under these conditions. The number of exerted silks was modeled using a negative exponential function. The parameter trait minimum ear biomass (MEB) corresponds to the threshold in ear mass growth below which silks do no emerge from the husk. The potential number of silks defines the yield potential. The exponent of the function defines the rate of silk appearance per unit ear growth, which was modeled using an exponential function of thermal time and a stress factor directly proportional to the water supply to demand ratio. To account for the plant-to-plant variation in flowering time, growth and development of three ears were implemented. The weighted average of the emerged silks for these three ears was utilized to determine the final attainable harvest index. The onset of ear growth was set at vegetative stage fifteen. Yields were simulated using a daily increment in harvest index, which was updated from the potential harvest index (Muchow et al., 1990) to that determined at flowering time based on the effects of water deficit on ear growth and silk emergence.

Approximate Bayesian Computation (ABC)

Five traits were identified as key components of the CGM for investigation within the ABC framework; Total Leaf Number (TLN), area of the largest leaf (AM), vapor pressure deficit value (breakpoint) above which transpiration is reduced below its potential (VPDB), minimum ear biomass for silk exertion (MEB), and cumulative thermal units from completion of canopy development, as measured by the completion of flag leaf expansion, and the timing of pollen shed (TUS). Together the traits TLN and AM influence canopy size, which influences soil water balance in water-limited environments. The trait VPDB influences transpiration rate of the canopy and can also influence soil water balance. The trait MEB influences reproductive resiliency and ultimately kernel set when water limitations coincide with the flowering period. TUS allowed for a source of genetic variation for flowering time, other than that associated with the variation for TLN.

The five traits were treated as latent variables for prediction by the CGM-WGP methodology. The latent value for each trait for each DH entry was modeled as a linear function of trait specific marker effects:

$$y\text{TLN}_i = \mu_{TLN} + z_i u_{TLN}$$

$$y\text{AM}_i = \mu_{AM} + z_i u_{AM}$$

$$y\text{VPDB}_1 = \mu_{VPDB} + z_i u_{VPDB}$$

$$y\text{MEB}_i = \mu_{MEB} + z_i u_{MEB}$$

$$y\text{TUS}_1 = \mu_{TUS} + z_i u_{TUS}$$

where $z_i$ is the vector of the observed biallelic SNP markers of DH entry i, $\mu_{TLN}$, $\mu_{AM}$, $\mu_{VPDB}$, $\mu_{MEB}$ and $\mu_{TUS}$ are the intercepts for the five traits and $u_{TLN}$, $u_{AM}$, $u_{VPDB}$, $u_{MEB}$ and $u_{TUS}$ the vectors of marker effects. The symbol θ was used to denote the joint parameter vector $[\mu_{TLN}, \ldots \mu_{TUS}, u_{TLN}, \ldots u_{TUS}]$.

Defining Prior Information for CGM Traits

Independent Normal distribution priors were used for the five traits for all components of θ. The prior for the intercepts $\mu_{TRAIT}$ was $N(m_{TRAIT}, \sigma_{\mu TRAIT}^2)$, where $m_{TRAIT}$ is the prior mean and $\sigma_{\mu TRAIT}^2$ the prior variance, which quantifies uncertainty in the intercept. The prior for the marker effects $u_{TRAIT}$ was $N(0, \sigma_{uTRAIT}^2)$, where the variance parameter $\sigma_{uTRAIT}^2$ controls the shrinkage of the marker effects towards 0. This prior corresponds to the BayesC prior. The $m_{TRAIT}$, $\sigma_{\mu TRAIT}^2$ and $\sigma_{uTRAIT}^2$ values for the five traits are given in Table 4.

TABLE 4

Prior parameter values for the five traits identified to influence grain yield in the two drought environments and treated as sources of genetic variation within the crop growth mode used within the CGM-WGP methodology

| | TRAIT | | | | |
|---|---|---|---|---|---|
| | TLN | AM | VPDB | MEB | TUS |
| $m_{TRAIT}$ | 19.37 | 842.90 | 1.90 | 0.76 | 40.00 |
| $\sigma_{\mu TRAIT}^2$ | 0.01 | 2.00 | 0.1 | 0.001 | 5.00 |
| $\sigma_{uTRAIT}^2$ | $0.016^2$ | 7.19 | $0.022^2$ | $0.005^2$ | 0.176 |

Different sources of information were used to obtain the prior values for the five traits. For TLN, AM and MEB a subset of 38 of the 106 DH lines was evaluated for TLN, AM and MEB in an experiment conducted in Iowa. The data for these three traits were obtained using the same testcross seed source used to obtain the grain yield data. As for grain yield the trait measurements were analyzed using a mixed model and BLUPs were obtained for the DH lines. For the traits TLN, AM and MEB, $m_{TRAIT}$ was then computed as the average of the measurements that were taken on the subset of 38 DHs included in the Iowa experiment. Also for these three traits $\sigma_{uTRAIT}^2$ was computed as var(TRAIT)/M, where var(TRAIT) is the observed variance of the measurements in the Iowa experiment and M the number of markers.

For the traits VPDB and TUS no direct measurements were made on the DH entries. All information used to define the prior parameters was based on published information for maize. For the VPDB trait the results reported by Gholipoor et al. (2013) were used. For TUS the prior parameters were determined based on a combination of published information indicating a TUS interval of 3 days (Muchow et al., 1990) and field observations indicating synchronous termination of leaf expansion and commencement of shedding for drought tolerant hybrids.

The ABC was implemented as described above. The simulation model operator Model($y^*_{ik}|\theta$) comprised the CGM $F(.)_{ik}$ as the deterministic component and a Gaussian noise variable distributed as $N(0, \sigma_\varepsilon^2)$ as the stochastic component. The value of $\sigma_\varepsilon^2$ was set equal to 5% of the observed variance of the grain yield BLUPs. The tolerance level was tuned to an acceptance rate of approximately $1 \cdot 10^{-6}$. The number of posterior samples drawn was 400. The CGM-WGP algorithm was implemented as a C routine integrated with the R software environment, R Core Team (2014).

CGM-WGP Estimation, Prediction and Testing Procedure

The CGM-WGP models were fitted and parameter estimates obtained using either data from the FS or SFS environment. A random set of 50 DH entries was used as the training set, referred to from hereon as the estimation set. The remaining 56 DH entries were then used to test the model performance and are referred to as the test set. The environment from which the data were sampled to fit the CGM-WGP model will be referred to as the estimation environment. The other environment will be referred to as the new environment. For the purposes of this paper the other environment is new in the sense that no data from that environment were used to select the CGM-WGP model or estimate the parameters. The selected CGM-WGP model was then tested in both the estimation environment and the new environment; e.g. the model was selected based on the sample of 50 DH entries in the FS environment, in this case the FS environment is the estimation environment and the SFS environment is the new environment, and then was tested on the remaining 56 DH entries in the FS estimation environment and the SFS new environment. Once the CGM-WGP model was selected the parameter estimates were used to predict yield of the DH entries for both the estimation and test sets in both the FS and SFS environments. Predictions for the same environment as the estimation environment will be referred to as observed environment predictions (e.g., predictions for FS with models fitted with FS data). Predictions for an environment from which no data were used in fitting the model will be referred to as new environment predictions (e.g., predictions for SFS with models fitted with FS data). This process was replicated 20 times for the FS and SFS environments. As a point estimate for the predicted grain yield of a DH entry in a specific environment we used the mean of the posterior predictive distribution for the DH entry in question. The posterior predictive distribution was obtained by evaluating the CGM $F(.)_{ik}$ over the accepted θ samples, using the weather, soil, irrigation and management data for that environment.

Prediction accuracy for the CGM-WGP was computed as the Pearson product moment correlation between predicted and observed performance of the DH entries in the environment for which the prediction was made. As a performance benchmark genomic best linear unbiased prediction (GBLUP; Meuwissen et al. 2001) was also applied to all data sets.

Results

The irrigation schedule applied to the two experiments resulted in similar temporal patterns of water deficit over the course of the experiments (FIG. 18). The period of maximum water deficit coincided with the timing of flowering for the DH entries in both experiments. Analysis of variance for the grain yield data indicated that there was significant genotypic variation among the DH entries (FIG. 19). There was also significant genotypic variation for the timing of flowering, as measured by heat units from planting to pollen shed (GDUSHD). However, there was no linear or non-linear association between GDUSHD and grain yield in the two environments (P>0.05). Therefore, variation for flowering time was not considered to have a direct impact on grain yield for the progeny of the chosen cross in the two drought environments. Therefore, while a component of the variation for grain yield variation could still be associated with flowering time effects conditional on other traits, the major component of grain yield variation for the DH entries was considered to be associated with trait variation other than timing of flowering. The GEI for grain yield between the two environments was significant. The GEI component of variance was smaller than the genotypic component of variance (FIG. 19). The genetic correlation for grain yield between the two environments, while less than 1.0, was estimated to be relatively high; 0.86. A component of the detected GEI for grain yield was associated with heterogeneity in the magnitude of genotypic variance between the two environments. A scatter plot comparing the grain yield BLUPs between the two environments indicated that there were some differences, but overall general agreement in the relative yield of the DH entries between the two environments (FIG. 19). Given these grain yield results the data set was considered suitable for evaluation of the CGM-WGP methodology. It is noted that the relatively low levels of change in rank of the DH entries between the two environments is expected to improve the chances of successful prediction between the environments for the GBLUP in comparison to other situations where greater levels of rank change occur between the environments. Exploration of a wider range of GEI scenarios than the single example shown in FIG. 19 is discussed further below. Here we focus on the requirements for the successful implementation of the CGM-WGP method for an empirical data set generated as part of a breeding program.

The initial set of environmental inputs that were used to run the CGM-WGP resulted in poor agreement between the grain yield predictions and observed results within the SFS environment. The predicted yield values were consistently lower than the observed yields. This resulted in a re-evaluation of the environmental inputs for the two environments. The initial assumption was that the soil depth for the adjacent fields was the same and the different yield levels would be explained by the different irrigation schedules used for the two environments. Further investigation of the characterization of the soils for the two adjacent fields revealed that there was a significant (P<0.001) difference in soil depth of approximately 0.2 m between the adjacent fields. Once this adjustment was made to the inputs for the CGM the predicted yields for the SFS environment aligned with the observed yields. This is provided as an example of some of the additional requirements associated with applying the CGM-WGP in practice. While this may be seen as an additional cost it also demonstrates that the CGM-WGP is responsive to the environmental inputs, a requirement to accommodate the effects of GEI.

Average prediction accuracy was positive for all CGM-WGP scenarios considered (Table 5). This result demonstrates that the CGM and the five traits TLN, AM, MEB, VPDB, and TUS provided a relevant framework to define models that capture genetic variation for yield in the form of the approximate posterior distributions of the parameters of θ obtained by applying the ABC algorithm.

TABLE 5

Prediction accuracy obtained for the CGM-WGP and GBLUP methods for grain yield of DH entries evaluated as testcross hybrids in two drought environments (FS and SFS), averaged over replications. For each replication the 106 DH entries belonged to either the Estimation set (50 DH entries) or Test set (56 DH entries). For each implementation the two environments were defined as either the Estimation environment or the Prediction environment.

| Estimation Environment | Prediction Environment | Estimation DH Entries | | Test DH Entries | |
| --- | --- | --- | --- | --- | --- |
| | | CGM-WGP | GBLUP | CGM-WGP | GBLUP |
| FS | FS | 0.82 | 0.78 | 0.23 | 0.24 |
| | SFS | 0.53 | 0.51 | 0.21 | 0.21 |
| SFS | FS | 0.50 | 0.53 | 0.22 | 0.23 |
| | SFS | 0.77 | 0.82 | 0.38 | 0.41 |

The highest prediction accuracy was achieved for the scenarios where the Estimation and Prediction environments were the same. This was the case for both the Estimation and Test sets of DH entries. This result is expected since predictions within an environment do not have to accommodate the effects of any GEI that occur between different environments.

The prediction accuracy was consistently higher when the CGM-WGP was applied to the Estimation set of DH entries in comparison to the application of the CGM-WGP to the Test set of DH entries (Table 5). Thus, there was loss of model adequacy for purposes of prediction when the selected parameters of θ were applied to new DH entries sampled from the same reference population. This loss of predictive skill occurred whether the Estimation and Prediction environments were the same (i.e., FS to FS and SFS to SFS) or different (i.e., FS to SFS and SFS to FS).

Figure 21B:
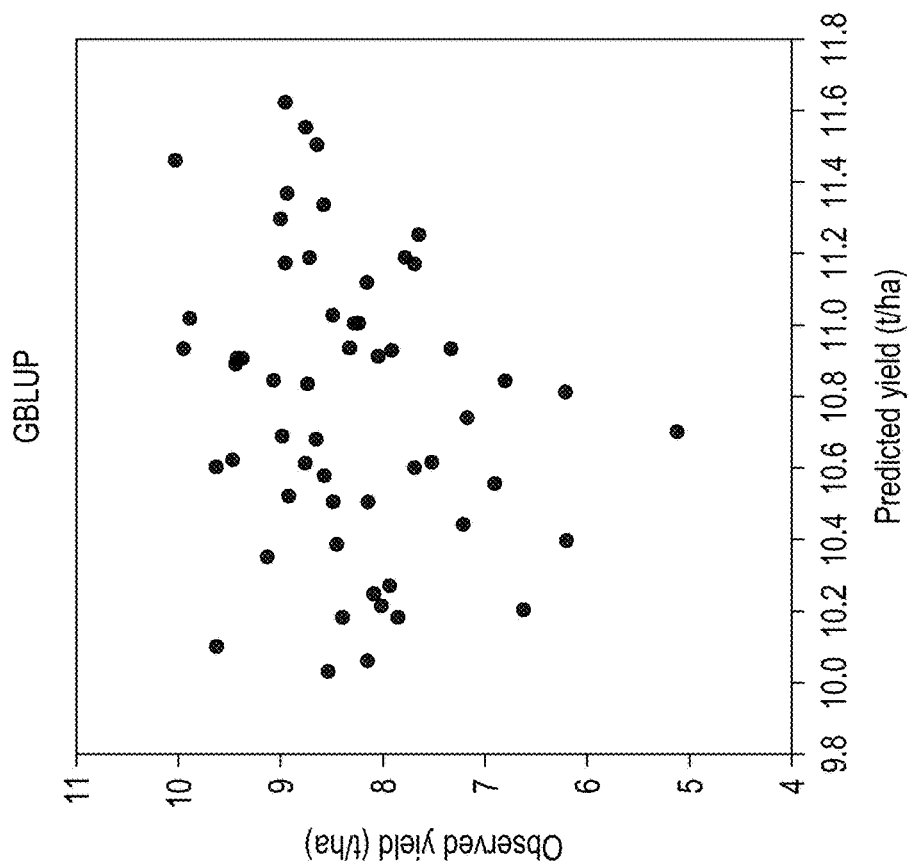
Figure 21A:
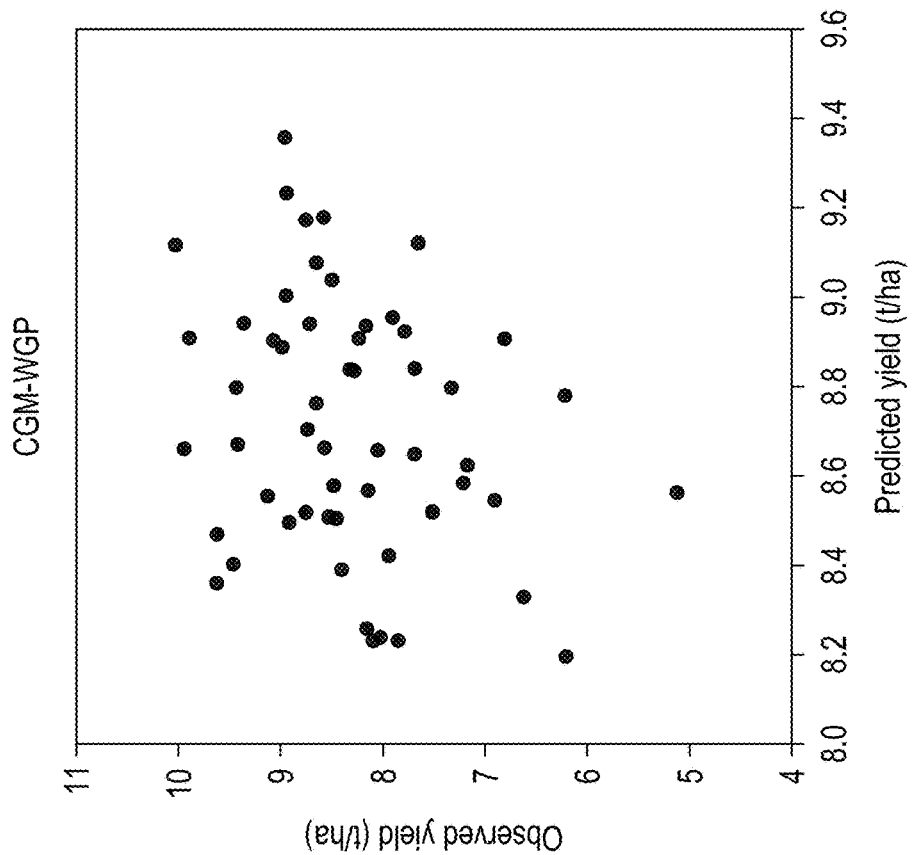

The average prediction accuracy for grain yield achieved by CGM-WGP was similar to that for GBLUP for all scenarios considered (Table 5). While average prediction accuracy was similar there were differences in prediction accuracy between CGM-WGP and GBLUP for individual replications (FIG. 20). These differences indicate that different genetic models for yield were selected by the CGM-WGP and GBLUP methods when they were applied to the same estimation data sets. A consequence of the selection of different genetic models by the two prediction methods was that yield predictions for different DH entries changed with the prediction method and the ranking of the individual DH entries could also change based on the predictions (FIG. 21). To further investigate the differences in the yield predictions for individual DH entries the yield predictions can be compared for each replication (FIG. 22). Thus, depending on the selection intensities applied by the breeder different sets of DH entries could be selected even though the average prediction accuracies were similar for both prediction methods. Another important difference between CGM-WGP and GBLUP was the adjustment of the scale of the grain yield predictions between the environments. The CGM-WGP method dynamically adjusted the scale of the yield predictions when moving between the two environments and consequently the mean value of the CGM-WGP yield predictions is close to the mean of the observed yield values (FIG. 21a). These adjustments are enabled through the relationships among the traits and the environmental variables that are included in the CGM. The GBLUP methodology does not have any relationship between the selected model parameters for yield and the environmental variables that changed between the two environments. Therefore, there is no adjustment to the scale of the yield predictions obtained by the GBLUP method when the estimation and test environments differ and the mean value of the GBLUP yield predictions can deviate from the mean of the observed yield values (FIG. 21b).

Example 8: Biological Model Based WGP Applied to Human Genetics

The mathematical model of human kidney function described by Goldstein and Rypins (1992) was used as a biological model to describe urinary sodium excretion (UNa, mEq/l) in humans as a function of the physiological traits mean arterial blood pressure (MAP, mmHg), aldosterone concentration (ALD, ng/l) and serum sodium (SNa, mEq/l). The physiological trait values were within the following ranges: MAP [50,120], ALD [40,125] and SNa [139.75,140.25]. FIG. 23 shows the observed relationships between UNa and these physiological traits.

The kidney model is henceforth denoted as $$F(y_{MAP_i}, y_{ALD_i}, y_{SNa_i})$$

where $y_{MAP_i}$ etc. are the values of the mentioned physiological traits. For brevity, this notation will be simplified to $F(\bullet)_i$.

Population, Genetic and Phenotypic Data

The synthetic human population consisted of 1,550 individuals. For the genomes only one chromosome with genetic length 0.596 Morgan (M) was considered. This is equal to the genetic length of human chromosome 21 (Dib et al., 1996). The chromosome was populated with 130 biallelic loci. Genotypes were generated stochastically in such a way that the linkage disequilibrium (LD) between markers (measured as r2) decayed exponentially with half-life equal to 0.03 M (FIG. 24). This mirrored the rapid LD decay observed in human genomes (Goddard and Hayes, 2009). The minor allele frequency ranged from 0.35 to 0.50 with an average of 0.42. The heterozygosity rate was close to 50%.

A random sample of 30 loci were assumed to be causative for the three physiological traits described above (the number of loci per trait was 10). These loci were masked in all subsequent analyses and thus assumed to be unobserved. The remaining 100 loci were treated as observed single nucleotide polymorphism (SNP) markers.

The additive substitution effects of the causative loci were drawn from a Standard Gaussian distribution. Raw genetic scores for the physiological traits were computed by summing these effects according to the observed genotypes at the loci for each of the 1,550 individuals. These raw scores were subsequently re-scaled linearly to the ranges mentioned before. Finally, the observed UNa values of all 1,550 individuals by using the physiological trait values were generated as inputs into $F(\bullet)_i$.

Statistical Model and Approximate Bayesian Computation (ABC)

The physiological traits MAP and ALD were assumed unknown and treated as hidden variables. They were modeled as linear functions of the trait specific marker effects $$y_{MAP_i} = \mu_{MAP} + z_i u_{MAP}$$

$$y_{ALD_i} = \mu_{ALD} + z_i u_{ALD}$$

where $z_i$ is the genotype vector of the observed SNP markers of individual i, $\mu_{MAP}$ etc. denote the intercepts and $u_{MAP}$ etc. the marker effects. For brevity, $\theta$ will be used to denote the joint parameter vector $[\mu_{MAP}, \mu_{ALD}, u_{MAP}, u_{ALD}]$.

Independent Gaussian distribution priors were used for all components of $\theta$. The prior for the intercept $\mu_{TRAIT}$ was $N(m_{TRAIT}, \sigma_{\mu_{TRAIT}}^2)$. To simulate imperfect prior information, the prior mean, $m_{TRAIT}$, was drawn from a Uniform distribution over the interval [0.9·TRAIT, 1.1·TRAIT], where TRAIT is the observed population mean of the physiological trait in question (either MAP or ALD). The prior variance $\sigma_{\mu_{TRAIT}}^2$ was equal to 25.0 for MAP and ALD. The prior for the marker effects $u_{TRAIT}$ was $N(0, \sigma_{u_{TRAIT}}^2)$. The value of $\sigma_{u_{TRAIT}}^2$ was determined by drawing from a Uniform distribution over the interval [0.9·var(TRAIT)/m, 1.1·var(TRAIT)/m], where m is the number of markers and var(TRAIT) the observed population variance of the physiological trait in question.

Serum sodium ($y_{SNa_i}$) was set to a constant value of 140.0 and not modeled. This trait thus served as a source of residual variation that cannot be captured by the model.

The ABC algorithm was used as described in previous examples. The simulation model operator Model(UNa|θ) comprised the kidney model $F(\bullet)_i$ as the deterministic component and a Gaussian noise variable distributed as $N(0, \sigma_e^2)$ as stochastic component. The value of $\sigma_e^2$ was set equal to 5% of the observed variance of the UNa values. The tolerance level was chosen such that the maximum acceptance rate was below $10^{-7}$. The number of posterior samples drawn was 100 or larger. This ABC based WGP method that incorporates the kidney model will be referred to as Kidney-WGP. The Kidney-WGP algorithm was implemented as a C routine integrated with the R software environment (R Core Team, 2014).

Estimation, Prediction and Testing Procedure

A random subset of N=100 individuals was used as estimation set. The remaining 1,450 individuals were used for testing model performance. As a point estimate for predicted UNa, we used the mean of the posterior predictive distribution for the individual in question. The posterior predictive distribution was obtained by evaluating $F(\bullet)_i$ over the accepted θ samples. Prediction accuracy was computed as the Pearson correlation between predicted and true performance. As a performance benchmark we used genomic best linear unbiased prediction (GBLUP, Meuwissen et al. (2001)). This procedure was repeated for 8 independently generated data sets.

Results

The biological-model based Kidney-WGP method had consistently higher average prediction accuracy within the estimation set than the benchmark method GBLUP (Table 1). This demonstrated that it did result in a better data fit. Kidney-WGP also had higher average prediction accuracy within the test set. While the differences were smaller, they were consistent, with Kidney-WGP having a higher accuracy than GBLUP in 6 out of 8 cases (see Table 1 for average prediction accuracy and FIG. 25 for predicted vs. observed values in an example replication).

TABLE 1

Prediction accuracy for human urinary sodium excretion (UNa, mEq/l) individuals in the estimation and test set averaged over 8 replications, for the biological-model based whole genomic prediction method (Kidney-WGP) and the benchmark method (GBLUP).

| Estimation set | | Test set | |
| --- | --- | --- | --- |
| Kidney-WGP | GBLUP | Kidney-WGP | GBLUP |
| 0.81 | 0.72 | 0.35 | 0.34 |

The invention claimed is:

1. A method for selecting individuals in a breeding program, said method comprising:
   a. growing a genetically diverse population of training individuals, wherein said training individuals are plants;
   b. phenotyping the genetically diverse population of training individuals to generate a phenotype training data set;
   c. associating the phenotype training data set with a genotype training data set comprising genetic information across the genome of each training individual, integrating a crop growth model into a rejection sampling algorithm for estimation of genotypic marker effects and linking the estimation of effects of genotypic markers with the crop growth model to generate an association training data set;
   d. genotyping a genetically diverse population of breeding individuals, wherein said breeding individuals are plants;
   e. selecting breeding pairs from the genetically diverse population of breeding individuals based genotypes using the association training data set and the crop growth model, estimating effects of genotypic markers and linking the estimation of effects of genotypic markers with the crop growth model to select breeding pairs likely to generate offspring with one or more desired traits;
   f. crossing the breeding pairs to generate offspring; and
   g. growing the offspring with the one or more desired traits.

2. The method of claim 1, further comprising crossing said selected breeding individuals.

3. The method of claim 1, wherein said genotypic information for the individual is obtained via genotyping using SNP markers.

4. The method of claim 1, wherein said breeding individuals are homozygous.

5. The method of claim 1, wherein said breeding individuals are plants.

6. The method of claim 5, wherein said plant is selected from the group consisting of: maize, soybean, sunflower, sorghum, canola, wheat, alfalfa, cotton, rice, barley, millet, sugar cane and switchgrass.

7. The method of claim 1, wherein said breeding individuals are animals.

8. The method of claim 1, wherein the method is applied to plant breeding.

9. The method of claim 1, wherein the method is applied to animal breeding.

10. The method of claim 5, further comprising a genetically diverse population that includes individuals carrying one or more transgenes.

11. The method of claim 5, further comprising a genetically diverse population that includes individuals with DNA edited with Cas9.

12. The method of claim 1, wherein said genotypic information for the individual is obtained by analyses of gene expression, metabolite concentration, or protein concentration.

13. The method of claim 1, wherein the rejection sampling algorithm is an approximate Bayesian computation algorithm.

14. The method of claim 1, wherein the crop growth model incorporates environmental and/or plant management information.

15. The method of claim 1, wherein the crop growth model incorporates elements that model the dynamics of plant processes.

16. The method of claim 1, wherein the crop growth model models the functional relationship between a complex trait and underlying component traits.

* * * * *